(12) United States Patent
Quirk

(10) Patent No.: US 7,179,603 B2
(45) Date of Patent: Feb. 20, 2007

(54) DETECTION AND IDENTIFICATION OF ENTERIC BACTERIA

(75) Inventor: Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 472 days.

(21) Appl. No.: 10/688,108

(22) Filed: Oct. 17, 2003

(65) Prior Publication Data

US 2004/0063139 A1    Apr. 1, 2004

Related U.S. Application Data

(62) Division of application No. 09/991,552, filed on Nov. 21, 2001, now Pat. No. 6,696,254.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.32

(58) Field of Classification Search ............... 435/6, 435/91.2; 536/24.32
See application file for complete search history.

(56) References Cited

U.S. PATENT DOCUMENTS

| | | | |
|---|---|---|---|
| 3,893,889 A | 7/1975 | Warren et al. ............... 195/100 |
| 4,070,247 A | 1/1978 | Burt ............................ 195/100 |
| 4,258,130 A | 3/1981 | Ashton et al. .................. 435/7 |
| 4,486,539 A | 12/1984 | Ranki et al. ................. 436/504 |
| 4,603,108 A | 7/1986 | Bascomb ..................... 435/34 |
| 4,677,055 A | 6/1987 | Dodin et al. ................... 435/7 |
| 4,689,295 A | 8/1987 | Taber et al. ................... 435/6 |
| 4,745,075 A | 5/1988 | Hadfield et al. ............. 436/523 |
| 4,935,339 A | 6/1990 | Zahradnik ..................... 435/5 |
| 5,169,757 A | 12/1992 | Yamazaki et al. ............. 435/7 |
| 5,198,339 A | 3/1993 | Hansen et al. ............... 435/7.2 |
| 5,225,330 A | 7/1993 | Ginsburg et al. .......... 435/7.32 |
| 5,306,466 A | 4/1994 | Goldsmith .................... 422/58 |
| 5,348,867 A | 9/1994 | Georgiou et al. .......... 435/69.7 |
| 5,354,661 A | 10/1994 | Doyle et al. .............. 435/7.37 |
| 5,356,778 A | 10/1994 | Hansen et al. ............... 435/7.2 |
| 5,397,698 A | 3/1995 | Goodman et al. ............. 435/6 |
| 5,405,754 A | 4/1995 | Calva-Mercado et al. .... 435/34 |
| 5,415,997 A | 5/1995 | Atrache et al. ............ 435/7.35 |
| 5,437,978 A | 8/1995 | Ubukata et al. ............... 435/6 |
| 5,447,836 A | 9/1995 | Wolber et al. ................. 435/4 |
| 5,468,613 A | 11/1995 | Erlich et al. ................... 435/6 |
| 5,472,846 A | 12/1995 | Rotman ..................... 435/7.23 |
| 5,491,068 A | 2/1996 | Benjamin et al. .......... 435/7.32 |
| 5,510,241 A | 4/1996 | Thorns ....................... 435/7.3 |
| 5,510,242 A | 4/1996 | Blais et al. ................ 435/7.32 |
| 5,529,910 A | 6/1996 | Ohashi et al. ............. 435/91.2 |
| 5,552,294 A | 9/1996 | Thorne ..................... 435/7.32 |
| 5,612,186 A | 3/1997 | Huang et al. .............. 435/7.37 |
| 5,618,666 A | 4/1997 | Popoff et al. .................. 435/6 |
| 5,620,845 A | 4/1997 | Gould et al. .................. 435/5 |
| 5,654,144 A | 8/1997 | Mann et al. ................... 435/6 |
| 5,660,981 A | 8/1997 | Grosz et al. ..................... 43/6 |
| 5,695,946 A | 12/1997 | Benjamin et al. .......... 435/7.32 |
| 5,733,724 A | 3/1998 | Bubert et al. .................. 435/6 |
| 5,741,662 A | 4/1998 | Madsen et al. ............... 435/34 |
| 5,747,272 A | 5/1998 | O'Brien et al. ............ 435/7.37 |
| 5,763,188 A | 6/1998 | Ohno et al. .................... 435/6 |
| 5,770,361 A | 6/1998 | Arthur et al. .................. 435/6 |
| 5,792,617 A | 8/1998 | Rotman ..................... 435/7.23 |
| 5,792,854 A * | 8/1998 | Lane et al. .............. 536/24.32 |
| 5,795,717 A | 8/1998 | Nakayama et al. ............ 435/6 |
| 5,804,378 A | 9/1998 | Popoff et al. .................. 435/6 |
| 5,807,694 A | 9/1998 | Zawistowski .............. 435/7.35 |
| 5,840,513 A | 11/1998 | Schubert et al. ........... 435/7.35 |
| 5,871,910 A | 2/1999 | Arthur et al. .................. 435/6 |
| 5,882,867 A | 3/1999 | Ullman et al. ................. 435/6 |
| 5,942,609 A | 8/1999 | Hunkapiller et al. ....... 536/25.3 |
| 5,958,686 A | 9/1999 | Houng ......................... 435/6 |
| 5,981,171 A | 11/1999 | Kuhns ........................... 435/5 |
| 5,989,841 A | 11/1999 | Popoff et al. .............. 435/7.35 |
| 6,004,766 A | 12/1999 | Atrache et al. ............ 435/7.94 |
| 6,060,256 A | 5/2000 | Everhart et al. ........... 435/7.21 |
| 6,077,668 A | 6/2000 | Kool ............................ 435/6 |
| 6,083,683 A | 7/2000 | Pace et al. ..................... 435/4 |
| 6,087,106 A | 7/2000 | Arthur et al. .................. 435/6 |

FOREIGN PATENT DOCUMENTS

| | | |
|---|---|---|
| GB | 2234587 A | 2/1991 |
| JP | 3-063571 A | 3/1991 |
| WO | WO98/42875 | 10/1998 |

OTHER PUBLICATIONS

Accession No. AF029556 (Aug. 2000).*
Accession No. BB242553 (Jul. 2000).*
PCT Search Report for International Application No. PCT/US02/31323, (Feb. 24, 2002), 3 pages.
Neto, E. D., et al., "Shotgun Sequencing of the Human Transcriptome with ORF Expressed Sequence Tags", *PNAS*, 97(7) (Mar. 28, 2000),3491-3496.
Quirk, S., "Cloning, Purification, and Characterization of the *Shigella boydii* dGTP Triphosphohydrolase", *Journal of Biological Chemistry*, 272(1) (Jan. 3, 1997),332-336.
Quirk, S, et al., "Primary Structure of the Deoxyguanosine Triphosphate Triphosphohydrolase-Encoding Gene (dgt) of *Escherichia coli*", *Gene*, 89(1): (Apr. 1990),13-18.
Wong, R. Y., et al., "Sample Sequencing of a *Salmonella typhimurium* LT2 Lamda Library: Comparison to the *Escherichia coli* K12 Genome", *FEMS Microbiology Letters*,173(2), (1999),411-423.

(Continued)

*Primary Examiner*—Kenneth R. Horlick
(74) *Attorney, Agent, or Firm*—Schwegman, Lundberg, Woessner, & Kluth, P.A.

(57) ABSTRACT

The invention provides probes, antibodies and methods for detecting a gene that is only found in Enterobacteriaceae, the deoxyguanosine triphosphate triphosphohydrolase gene. These probes and methods are useful for the detecting whether test samples, including food and water samples, are infected with enteric bacteria.

11 Claims, 11 Drawing Sheets

OTHER PUBLICATIONS

Archer, Douglas L., "Contemporary Issue: Diseases with a Food Vector", *Clinical Microbiology Reviews*, vol. 1, No. 4,(Oct. 1988),377-398.

Beauchamp, Benjamin B., "A Unique Deoxyguanosine Triphosphate is Responsible for the . . . ", *Proceedings of the National Academy of Sciences*, vol. 85,(Apr. 1988),2563-2567.

Belgrader, Phillip , "Rapid Pathogen Detection Using a Microchip PCR Array Instrument", *Clinical Chemistry*, vol. 44, No. 10,(1998),2191-2194.

Bradford, Marion M., "A Rapid and Sensitive Method for the Quantitation of Microgram . . . ", *Analytical Biochemistry*, vol. 72,(1976),248-254.

Bradford, Marion M., "A Rapids and Sensative Method for the Quantitation of Microgram . . . ", *Analytical Biochemistry*, vol. 72,(1976),248-254.

Bunning, V. K., et al., "Chronic Health Effects of Microbial Foodbone Disease", *World Health Statistics Quarterly*, vol. 50, No. 1/2,(1997),51-56.

Dekeyser, P. , et al., "Acute Enteritis Due to Related Vibrio: First Positive Stool Cultures", *The Journal of Infectious Diseases*, vol. 125, No. 4,(Apr. 1972),390-392.

Dubs, Marie-Christine , "Interaction Between Viruses and Monoclonal Antibodies Studied . . . ", *Immunology Letters*, vol. 31, No. 1,(Jan. 1992),59-64.

Haedicke, W , et al., "Specific and Sensitive Two-Step Polymerase Chain Reaction Assay . . . ", *European Journal of Clinical Microbiology & Infectious Diseases*, vol. 15, No. 7,(Jul. 1996),603-607.

Jackson, Lisa A., "Listerosis: A Foodborne Disease", *Infections in Medicine*, vol. 10,(Feb. 1993),61-66.

Janda, J. M., "Infections Associated with the Genus *Edwardsiella*: the Role . . . ", *Clinical Infection Diseases*, vol. 17, No. 4,(Oct. 1993),742-748.

Kaferstein, F. K., "Foodborne Disease Control: A Transnational Challenge", *Emerging Infectious Diseases*, vol. 3, No. 4,(Oct./Dec. 1997),503-510.

Kaiser, Donald A., "Characterization of Actin and Poly-L-proline Binding Sites of . . . ", *Journal of Molecular Biology*, vol. 256,(1996),89-107.

Karlsson, Robert , et al., "Experimental Design for Kinetic Analysis of Protein-Protein Interactions With Surface Plasmon Resonance Biosensors", *Journal of Immunological Methods* 200 (1997) 121-133.

Karlsson, Robert , et al., "Kinetic Analysis of Monoclonal Antibody-Antigen Interactions . . . ", *Journal of Immunological Methods*, vol. 145,(Dec. 1991),229-240.

Korberg, S. R., et al., "Enzymatic Cleavage of Deoxyguanosine Triphosphate to . . . ", *The Journal of Biological Chemistry*, vol. 233,(1958),159-162.

Laemmli, U. K., "Cleavage of Structural Proteins during the Assembly of the Head . . . ", *Nature: International Journal of Science*, vol. 227,(1970),680-685.

Levasseur, Stephane , et al., "Rapid Detection of Members of the Family Enterobacteriaceae by . . . ", *Applied and Environmental Microbiology*, vol. 58, No. 5,(May 1992),1524-1529.

Li, Chuan , et al., "Disribution of an L-Isoaspartyl Protein Methyltransferase . . . ", *Journal of Bacteriology*, vol. 174, No. 2,(Jan. 1992),355-361.

Lindsay, James A., "Chronic Sequelae of Foodborne Disease", *Emerging Infectious Diseases*, vol. 3, No. 4,(Oct./Dec. 1997),443-452.

Lofas, Stefan , et al., "Methods for Site Controlled Coupling to Carboxymethyldextran . . . ", *Biosensors & Bioelectronics*, vol. 10,(1995),813-822.

Morton, Thomas , et al., "Interpreting Complex Binding Kinetics From Optical Biosensors: A Comparison of Analysis by Linearization, the Integrated Rate Equation, and Numerical Integration", *Analytical Biochemistry*, 227, 176-185 (1895).

Nakai, Hiroshi , et al., "The gene 1.2 Protein of Bacteriophage T7 Interacts with the . . . ", *The Journal of Biological Chemistry*, vol. 265, No. 8,(1990),4411-4419.

Nataro, James P., et al., "Enteroaggregative *Escherichia coli*", *Emerging Infectious Diseases*, vol. 4, No. 2,(Apr./Jun. 1998),251-261.

Northrup, M. A., et al., "A Miniature Analytical Instrument for Nucleic Acids Based on . . . ", *Analytical Chemistry*, vol. 70, No. 5,(Mar. 1998),918-922.

O'Shannessy, Daniel J., et al., "Determination of Rate and Equilibrium Binding Constants for Macromolecular Interactions Using Surface Plasmon Resonance: Use of Nonlinear Squares Analysis Methods", *Analytical Biochemistry*, 212, (1993),457-468.

Olsvik, Orjan , et al., "Pathogenic *Escherichia coli* Found In Food", *International Journal of Food Microbiology*, vol. 12,(1991), 103-114.

Quirk, Stephen , et al., "dGTP Triphosphohydrolase, a Unique Enzyme Confined to memerbs of the Family Enterbacteriaceae", *Journal of Bacteriology*, Nov. 1991, 6665-6669, 173(21).

Schaberg, Dennis R., et al., "Major Trends in the Mirobial Etiology of Nosocomial Infection", *The American Journal of Medicine*, vol. 91 (suppl 3B),(Sep. 1991),72S-75S.

Seto, Donald , et al., "The Purification and Properties of Deoxyguanosine Triphosphate . . . ", *The Journal of Biological Chemistry*, vol. 263, No. 3,(Jan. 1988),1494-1499.

Siegel, Lewis M., "Determination of Molecular Weights and Frictional Ratios of Proteins . . . ", *Biochemica Et Biophysica Acta*, vol. 112,(1966),346-362.

Sojka, Marcjanna G., et al., "Characterisation of Monoclonal Antibodies Specific to SEF 21 Fimbriae of *Salmonella enteritidis* and their Reactivity with Other Salmonellae and Enterobacteria", *Veterinary Microbiology*, vol. 48, Nos. 3 & 4,(Feb. 1996),207-221.

Towbin, Harry , et al., "Electrophoretic Transfer of Proteins from Polyacrylamide Gels to Nitrocellulose Sheets: Procedure and Some Applications", *Proceedings of the National Academy of Sciences*, (Sep. 1979),4350-4354.

Wurgler, Susannah M., et al., "Structure and Regulation of the Gene for dGTP triphosphohydrolase from *Escherichia coli*", *Proceedings of the National Academy of Sciences*, vol. 76, No. 9,(Apr. 1990),2740-2744.

\* cited by examiner

```
1                        .                        .                        .                        .                        .                        .                        .                        80
ATGGCACAGATTGATTTCCGAAAAAAAATAAACTGGCATCGTCGTTACCGTTCACCGCAGGGCGTTAAAACCGAACATGA
81                       .                        .                        .                        .                        .                        .                        .                       160
GATCCTGCGGATCTTCGAGAGCGATCGCGGGCGTATCATCAACTCTCCGGCAATTCGTCGTCTGCAACAAAAGACCCAGG
161                      .                        .                        .                        .                        .                        .                        .                       240
TTTTTCCACTGGAGCGCAATGCCGCCGTGCGCACGCGTCTTACCCACTCGATGGAAGTCCAGCAGGTGGGGCGCTACATC
241                      .                        .                        .                        .                        .                        .                        .                       320
GCCAAAGAAATTTTAAGCCGTCTGAAAGAGCTTAAATTACTGGAAGCATACGGCCTGGATGAACTGACCGGTCCCTTTGA
321                      .                        .                        .                        .                        .                        .                        .                       400
AAGCATTGTTGAGATGTCATGCCTGATGCACGATATCGGCAATCCGCCGTTTGGTCATTTTGGCGAAGCGGCGATAAATG
401                      .                        .                        .                        .                        .                        .                        .                       480
ACTGGTTTCGCCAACGTTTGCACCCGGAAGATGCCGAAAGCCAGCCTCTGACTGACGATCGCTGCAGCGTGGCGGCACTA
481                      .                        .                        .                        .                        .                        .                        .                       560
CGTTTACGGGACGGGGAAGAACCGCTTAACGAGCTGCGGCGCAAGATTCGTCAGGACTTATGTCATTTTGAGGGGAATGC
561                      .                        .                        .                        .                        .                        .                        .                       640
ACAAGGCATTCGCCTGGTGCATACATTGATGCGGATGAATCTCACCTGGGCACAGGTTGGCGGTATTTTAAAATATACCC
641                      .                        .                        .                        .                        .                        .                        .                       720
GTCCGGCGTGGTGGCGTGGCGAAACGCCTGAGACACATCACTATTTAATGAAAAAGCCGGGTTATTATCTTTCTGAAGAA
721                      .                        .                        .                        .                        .                        .                        .                       800
GCCTATATTGCCCGGTTGCGTAAAGAACTTAATTTGGCGCTTTACAGTCGTTTTCCATTAACGTGGATTATGGAAGCTGC
801                      .                        .                        .                        .                        .                        .                        .                       880
CGACGACATCTCCTATTGTGTGGCAGACCTTGAAGATGCGGTAGAGAAAAGAATATTTACCGTTGAGCAGCTTTATCATC
881                      .                        .                        .                        .                        .                        .                        .                       960
ATTTGCACGAAGCGTGGGGCCAGCATGAGAAAGGTTCGCTCTTTTCGCTGGTGGTTGAAAATGCCTGGGAAAAATCACGC
961                      .                        .                        .                        .                        .                        .                        .                      1040
TCAAATAGTTTAAGCCGCAGTACGGAAGATCAGTTTTTTATGTATTTACGGGTAAACACCCTAAATAAACTGGTACCCTA
1041                     .                        .                        .                        .                        .                        .                        .                      1120
CGCGGCACAACGATTTATTGATAATCTGCCTGCGATTTTCGCCGGAACGTTTAATCATGCATTATTGGAAGATGCCAGCG
1121                     .                        .                        .                        .                        .                        .                        .                      1200
AATGCAGCGATCTTCTTAAGCTATATAAAAATGTCGCTGTAAAACATGTGTTTAGCCATCCAGATGTCGAGCGGCTTGAA
1201                     .                        .                        .                        .                        .                        .                        .                      1280
TTGCAGGGCTATCGGGTCATTAGCGGATTATTAGAGATTTATCGTCCTTTATTAAGCCTGTCGTTATCAGACTTTACTGA
1281                     .                        .                        .                        .                        .                        .                        .                      1360
ACTGGTAGAAAAAGAACGGGTGAAACGTTTCCCTATTGAATCGCGCTTATTCCACAAACTCTCGACGCCGCATCGGCTGG
1361                     .                        .                        .                        .                        .                        .                        .                      1440
CCTATGTCGAGGCTGTCAGTAAATTACCGTCAGATTCTCCTGAGTTTCCGCTATGGGAATATTATTACCGTTGCCGCCTG
1441                     .                        .                        .                        .                        .                        .                        .                      1518
CTGCAGGATTATATCAGCGGTATGACCGACCTCTATGCGTGGGATGAATACCGACGTCTGATGGCCGTAGAACAATAA
```

FIG. 9

SEQUENCE LISTING

<160> NUMBER OF SEQ ID NOS: 36

<210> SEQ ID NO 1
<211> LENGTH: 1518
<212> TYPE: DNA
<213> ORGANISM: Escherichia coli

<400> SEQUENCE: 1

| | | | | | | |
|---|---|---|---|---|---|---|
| atggcacaga | ttgatttccg | aaaaaaaata | aactggcatc | gtcgttaccg | ttcaccgcag | 60 |
| ggcgttaaaa | ccgaacatga | gatcctgcgg | atcttcgaga | gcgatcgcgg | gcgtatcatc | 120 |
| aactctccgg | caattcgtcg | tctgcaacaa | aagacccagg | tttttccact | ggagcgcaat | 180 |
| gccgccgtgc | gcacgcgtct | tacccactcg | atggaagtcc | agcaggtggg | gcgctacatc | 240 |
| gccaaagaaa | ttttaagccg | tctgaaagag | cttaaattac | tggaagcata | cggcctggat | 300 |
| gaactgaccg | gtcccttgta | aagcattgtt | gagatgtcat | gcctgatgca | cgatatcggc | 360 |
| aatccgccgt | ttggtcattt | tggcgaagcg | gcgataaatg | actggtttcg | ccaacgtttg | 420 |
| cacccggaag | atgccgaaag | ccagcctctg | actgacgatc | gctgcagcgt | ggcggcacta | 480 |
| cgtttacggg | acggggaaga | accgcttaac | gagctgcggc | gcaagattcg | tcaggactta | 540 |
| tgtcattttg | aggggaatgc | acaaggcatt | cgcctggtgc | atacattgat | gcggatgaat | 600 |
| ctcacctggg | cacaggttgg | cggtatttta | aaatataccc | gtccggcgtg | gtggcgtggc | 660 |
| gaaacgcctg | agacacatca | ctatttaatg | aaaaagccgg | gttattatct | ttctgaagaa | 720 |
| gcctatattg | cccggttgcg | taaagaactt | aatttggcgc | tttacagtcg | ttttccatta | 780 |
| acgtggatta | tggaagctgc | cgacgacatc | tcctattgtg | tggcagacct | tgaagatgcg | 840 |
| gtagagaaaa | gaatatttac | cgttgagcag | ctttatcatc | atttgcacga | agcgtggggc | 900 |
| cagcatgaga | aaggttcgct | cttttcgctg | gtggttgaaa | atgcctggga | aaaatcacgc | 960 |
| tcaaatagtt | taagccgcag | tacggaagat | cagtttttta | tgtatttacg | ggtaaacacc | 1020 |
| ctaaataaac | tggtacccta | cgcggcacaa | cgatttattg | ataatctgcc | tgcgattttc | 1080 |
| gccggaacgt | ttaatcatgc | attattggaa | gatgccagcg | aatgcagcga | tcttcttaag | 1140 |
| ctatataaaa | atgtcgctgt | aaaacatgtg | tttagccatc | cagatgtcga | gcggcttgaa | 1200 |
| ttgcagggct | atcgggtcat | tagcggatta | ttagagattt | atcgtccttt | attaagcctg | 1260 |
| tcgttatcag | actttactga | actggtagaa | aaagaacggg | tgaaacgttt | ccctattgaa | 1320 |
| tcgcgcttat | tccacaaact | ctcgacgccg | catcggctgg | cctatgtcga | ggctgtcagt | 1380 |
| aaattaccgt | cagattctcc | tgagtttccg | ctatgggaat | attattaccg | ttgccgcctg | 1440 |
| ctgcaggatt | atatcagcgg | tatgaccgac | ctctatgcgt | gggatgaata | ccgacgtctg | 1500 |
| atggccgtag | aacaataa | | | | | 1518 |

<210> SEQ ID NO 2
<211> LENGTH: 16
<212> TYPE: DNA
<213> ORGANISM: Artificial Sequence
<220> FEATURE:
<223> OTHER INFORMATION: A primer.

<400> SEQUENCE: 2
ccactggagc gcaatg                                                     16

<210> SEQ ID NO 3
<211> LENGTH: 17

-continued

```
<212> TYPE: DNA
<213> ORGANISM: Artificial Sequence
<220> FEATURE:
<223> OTHER INFORMATION: A primer.

<400> SEQUENCE: 3
tgcatcaggc atgacat                                                17

<210> SEQ ID NO 4
<211> LENGTH: 18
<212> TYPE: DNA
<213> ORGANISM: Artificial Sequence
<220> FEATURE:
<223> OTHER INFORMATION: A primer.

<400> SEQUENCE: 4
aaaatgacca aacggcgg                                               18

<210> SEQ ID NO 5
<211> LENGTH: 14
<212> TYPE: DNA
<213> ORGANISM: Artificial Sequence
<220> FEATURE:
<223> OTHER INFORMATION: A primer.

<400> SEQUENCE: 5
gggcgctaca tcgc                                                   14

<210> SEQ ID NO 6
<211> LENGTH: 16
<212> TYPE: DNA
<213> ORGANISM: Artificial Sequence
<220> FEATURE:
<223> OTHER INFORMATION: A primer.

<400> SEQUENCE: 6
aatgaccaaa cggcgg                                                 16

<210> SEQ ID NO 7
<211> LENGTH: 17
<212> TYPE: DNA
<213> ORGANISM: Artificial Sequence
<220> FEATURE:
<223> OTHER INFORMATION: A primer.

<400> SEQUENCE: 7
gctgcagcgt ggcggca                                                17

<210> SEQ ID NO 8
<211> LENGTH: 18
<212> TYPE: DNA
<213> ORGANISM: Artificial Sequence
<220> FEATURE:
<223> OTHER INFORMATION: A primer.

<400> SEQUENCE: 8
ctcaggcgtt tcgccacg                                               18

<210> SEQ ID NO 9
<211> LENGTH: 17
<212> TYPE: DNA
<213> ORGANISM: Artificial Sequence
<220> FEATURE:
<223> OTHER INFORMATION: A primer.

<400> SEQUENCE: 9
```
cccggaagat gccgaaa                                               17

<210> SEQ ID NO 10
<211> LENGTH: 17
<212> TYPE: DNA
<213> ORGANISM: Artificial Sequence
<220> FEATURE:
<223> OTHER INFORMATION: A primer.

<400> SEQUENCE: 10
cggttcttcc ccgtccc                                               17

<210> SEQ ID NO 11
<211> LENGTH: 17
<212> TYPE: DNA
<213> ORGANISM: Artificial Sequence
<220> FEATURE:
<223> OTHER INFORMATION: A primer.

<400> SEQUENCE: 11
gctgtgtggt ttcctcg                                               17

<210> SEQ ID NO 12
<211> LENGTH: 18
<212> TYPE: DNA
<213> ORGANISM: Artificial Sequence
<220> FEATURE:
<223> OTHER INFORMATION: A primer.

<400> SEQUENCE: 12
aatccggcac cggccctc                                              18

<210> SEQ ID NO 13
<211> LENGTH: 17
<212> TYPE: DNA
<213> ORGANISM: Artificial Sequence
<220> FEATURE:
<223> OTHER INFORMATION: A primer.

<400> SEQUENCE: 13
tccggaagat gcggaaa                                               17

<210> SEQ ID NO 14
<211> LENGTH: 17
<212> TYPE: DNA
<213> ORGANISM: Artificial Sequence
<220> FEATURE:
<223> OTHER INFORMATION: A primer.

<400> SEQUENCE: 14
attttcttca ccttcct                                               17

<210> SEQ ID NO 15
<211> LENGTH: 17
<212> TYPE: DNA
<213> ORGANISM: Artificial Sequence
<220> FEATURE:
<223> OTHER INFORMATION: A primer.

<400> SEQUENCE: 15
gctgcgaagt gcaggcc                                               17

<210> SEQ ID NO 16
<211> LENGTH: 18
<212> TYPE: DNA
<213> ORGANISM: Artificial Sequence -continued

```
<220> FEATURE:
<223> OTHER INFORMATION: A primer.

<400> SEQUENCE: 16
tggccggcgt ctcctcag                                                         18

<210> SEQ ID NO 17
<211> LENGTH: 17
<212> TYPE: DNA
<213> ORGANISM: Artificial Sequence
<220> FEATURE:
<223> OTHER INFORMATION: A primer.

<400> SEQUENCE: 17
gcccggcgat gcgctcg                                                          17

<210> SEQ ID NO 18
<211> LENGTH: 17
<212> TYPE: DNA
<213> ORGANISM: Artificial Sequence
<220> FEATURE:
<223> OTHER INFORMATION: A primer.

<400> SEQUENCE: 18
cgatgtctct ccgtcat                                                          17

<210> SEQ ID NO 19
<211> LENGTH: 496
<212> TYPE: PRT
<213> ORGANISM: Escherichia coli

<400> SEQUENCE: 19
```

Met Ala Gln Ile Asp Phe Arg Lys Lys Ile Asn Trp His Arg Arg Tyr
 1               5                  10                  15

Arg Ser Pro Gln Gly Val Lys Thr Glu His Glu Ile Leu Arg Ile Phe
            20                  25                  30

Glu Ser Asp Arg Gly Arg Ile Ile Asn Ser Pro Ala Ile Arg Arg Leu
        35                  40                  45

Gln Gln Lys Thr Gln Val Phe Pro Leu Glu Arg Asn Ala Ala Val Arg
    50                  55                  60

Thr Arg Leu Thr His Ser Met Glu Val Gln Gln Val Gly Arg Tyr Ile
65                  70                  75                  80

Ala Lys Glu Ile Leu Ser Arg Leu Lys Ser Leu Asn Thr Glu Leu Thr
                85                  90                  95

Gly Pro Phe Glu Ser Ile Val Glu Tyr Ala Cys Leu Met His Asp Ile
            100                 105                 110

Ala Ile Arg Arg Leu Val Ile Leu Ala Lys Arg Thr Ile Asn Asp Trp
        115                 120                 125

Phe Gly Gln Arg Leu His Pro Glu Asp Ala Glu Ser Gln Pro Leu Thr
    130                 135                 140

Asp Arg Cys Ser Val Ala Ala Leu Arg Leu Arg Thr Gly Lys Asn Arg
145                 150                 155                 160

Leu Thr Ser Cys Gly Ala Arg Phe Val Arg Thr Tyr Val Ile Leu Arg
                165                 170                 175

Gly Met His Lys His Ser Pro Gly Ala Tyr Ile Asp Ala Asp Glu Ser
            180                 185                 190

His Leu Gly Thr Gly Trp Arg Tyr Phe Lys Ile Tyr Pro Ser Gly Val
        195                 200                 205

Val Ala Cys Glu Thr Pro Glu Thr His His Tyr Leu Met Lys Lys Pro

-continued

```
                210                 215                 220
Gly Tyr Tyr Leu Ser Glu Glu Ala Tyr Ile Ala Arg Leu Arg Lys Glu
225                 230                 235                 240

Leu Asn Leu Ala Leu Tyr Ser Arg Phe Pro Leu Thr Trp Ile Met Glu
                245                 250                 255

Ala Ala Asp Asp Ile Ser Tyr Cys Val Ala Asp Leu Glu Asp Ala Val
                260                 265                 270

Glu Lys Arg Ile Phe Thr Val Glu Gln Leu Tyr His His Leu His Glu
            275                 280                 285

Ala Trp Gly Gln His Glu Lys Gly Ser Leu Phe Ser Leu Val Val Glu
290                 295                 300

Asn Ala Trp Glu Lys Ser Arg Ser Asn Ser Leu Ser Arg Ser Thr Glu
305                 310                 315                 320

Asp Gln Phe Phe Met Tyr Leu Arg Val Asn Thr Leu Asn Lys Leu Val
                325                 330                 335

Pro Tyr Ala Ala Gln Arg Phe Ile Asp Asn Leu Pro Ala Ile Phe Ala
                340                 345                 350

Gly Arg Phe Asn His Ala Leu Leu Glu Asp Ala Ser Glu Cys Ser Asp
            355                 360                 365

Leu Leu Lys Leu Tyr Lys Asn Val Ala Val Lys His Val Phe Ser His
370                 375                 380

Pro Asp Val Glu Arg Leu Glu Leu Gln Gly Tyr Arg Val Ile Ser Gly
385                 390                 395                 400

Leu Leu Glu Ile Tyr Arg Pro Leu Leu Ser Leu Ser Leu Ser Asp Phe
                405                 410                 415

Thr Glu Leu Val Glu Lys Glu Arg Val Lys Arg Phe Pro Ile Glu Ser
                420                 425                 430

Arg Leu Phe His Lys Leu Ser Thr Pro His Arg Leu Ala Tyr Val Glu
            435                 440                 445

Ala Val Ser Lys Leu Pro Ser Asp Ser Pro Glu Phe Pro Leu Trp Glu
450                 455                 460

Tyr Tyr Tyr Arg Cys Arg Leu Leu Gln Asp Tyr Ile Ser Gly Met Thr
465                 470                 475                 480

Asp Leu Tyr Ala Trp Asp Glu Tyr Arg Arg Leu Met Ala Val Glu Gln
                485                 490                 495
```

<210> SEQ ID NO 20
<211> LENGTH: 495
<212> TYPE: PRT
<213> ORGANISM: Salmonella typhimurium

<400> SEQUENCE: 20

```
Met Ala Ser Ile Asp Phe Arg Asn Lys Ile Asn Trp His Arg Arg Tyr
1               5                   10                  15

Arg Ser Pro Gln Gly Val Lys Thr Glu His Glu Ile Leu Arg Ile Phe
                20                  25                  30

Glu Ser Asp Arg Gly Arg Leu Ile Asn Ser Pro Ala Ile Arg Arg Leu
            35                  40                  45

Gln Gln Lys Thr Gln Val Phe Pro Leu Glu Arg Asn Ala Ala Val Arg
        50                  55                  60

Thr Arg Leu Thr His Ser Met Glu Val Gln Val Gly Arg Tyr Ile
65                  70                  75                  80

Ala Lys Glu Ile Leu Ser Arg Leu Lys Glu Gln Asp Arg Leu Glu Glu
                85                  90                  95
```

```
Tyr Gly Leu Asp Ala Leu Thr Gly Pro Phe Glu Ser Ile Val Glu Met
            100                 105                 110

Ala Cys Leu Met His Asp Ile Gly Asn Pro Pro Phe Gly His Phe Gly
        115                 120                 125

Glu Ala Ala Ile Asn Asp Trp Phe Arg Gln Arg Leu His Pro Glu Asp
    130                 135                 140

Ala Glu Ser Gln Pro Leu Thr His Asp Arg Cys Val Val Phe Ser Leu
145                 150                 155                 160

Arg Leu Gln Lys Tyr Val Arg Asp Ile Cys His Leu Lys Ala Cys Thr
                165                 170                 175

Arg Glu Phe Val Cys Thr Ile Arg Ser Cys Gly Gly Ile Leu Thr Trp
            180                 185                 190

Ala Ala Val Arg Pro Asn Phe Lys Asn Ile Pro Val Pro Ala Cys Trp
        195                 200                 205

Pro Arg Gly Arg Ser Arg Ile Pro Ile Arg Tyr Leu Met Lys Lys Pro
    210                 215                 220

Arg Tyr Tyr Leu Ser Glu Glu Lys Tyr Ile Ala Arg Leu Arg Lys Glu
225                 230                 235                 240

Leu Gln Leu Arg Pro Tyr Ser Arg Phe Pro Leu Thr Trp Ile Met Glu
                245                 250                 255

Ala Ala Asp Asp Ile Ser Tyr Cys Val Ala Asp Leu Glu Asp Ala Val
            260                 265                 270

Glu Lys Arg Ile Phe Ser Val Glu Gln Leu Tyr His His Leu Tyr His
        275                 280                 285

Ala Trp Cys His His Glu Lys Asp Ser Leu Phe Glu Leu Val Val Gly
    290                 295                 300

Asn Ala Trp Glu Lys Ser Arg Ala Asn Thr Leu Ser Arg Ser Thr Glu
305                 310                 315                 320

Asp Gln Phe Phe Met Tyr Leu Arg Val Asn Thr Leu Asn Lys Leu Val
                325                 330                 335

Pro Tyr Ala Gln Arg Phe Ile Asp Asn Leu Pro Gln Ile Phe Ala Gly
            340                 345                 350

Thr Phe Asn Gln Ala Leu Leu Glu Asp Ala Ser Gly Phe Ser Arg Leu
        355                 360                 365

Leu Glu Leu Tyr Lys Asn Val Ala Val Glu His Val Phe Ser His Pro
    370                 375                 380

Asp Val Glu Gln Leu Glu Leu Gln Gly Tyr Arg Val Ile Ser Gly Leu
385                 390                 395                 400

Leu Asp Ile Tyr Gln Pro Leu Leu Ser Leu Ser Leu Asn Asp Phe Arg
                405                 410                 415

Glu Leu Val Glu Lys Glu Arg Leu Lys Arg Phe Pro Ile Glu Ser Arg
            420                 425                 430

Leu Phe Gln Lys Leu Ser Thr Arg His Arg Leu Ala Tyr Val Glu Val
        435                 440                 445

Val Ser Lys Leu Pro Thr Asp Ser Ala Glu Tyr Pro Val Leu Glu Tyr
    450                 455                 460

Tyr Tyr Arg Cys Arg Leu Ile Gln Asp Tyr Ile Ser Gly Met Thr Asp
465                 470                 475                 480

Leu Tyr Ala Trp Asp Glu Tyr Arg Arg Leu Met Ala Val Glu Gln
                485                 490                 495

<210> SEQ ID NO 21
<211> LENGTH: 332
<212> TYPE: PRT
```

<213> ORGANISM: Klebsiella oxytoca

<400> SEQUENCE: 21

Met Ala Lys Ile Asp Phe Arg Asn Lys Ile Asn Trp Arg Arg Arg Phe
1               5                   10                  15
Arg Ser Pro Pro Arg Val Glu Thr Glu Arg Asp Ile Leu Arg Ile Phe
            20                  25                  30
Glu Ser Asp Arg Gly Arg Ile Val Asn Ser Pro Ala Ile Arg Arg Leu
        35                  40                  45
Gln Gln Lys Thr Gln Val Phe Pro Leu Glu Arg Asn Gly Arg Val Arg
    50                  55                  60
Thr Arg Leu Thr His Ser Leu Glu Val Gln Gln Val Gly Arg Tyr Ile
65                  70                  75                  80
Ala Lys Glu Val Leu Ser Arg Leu Lys Glu Leu Arg Leu Leu Glu Glu
                85                  90                  95
Tyr Gly Leu Glu Glu Leu Thr Gly Pro Phe Glu Ser Val Val Glu Met
            100                 105                 110
Ala Cys Leu Met His Asp Ile Gly Asn Pro Pro Phe Gly His Phe Gly
        115                 120                 125
Glu Ala Ala Ile Asn Asp Trp Phe Arg Gln Arg Leu Ala Pro Gly Asp
    130                 135                 140
Ala Leu Gly Gln Pro Leu Thr Asp Asp Arg Cys Glu Val Gln Ala Leu
145                 150                 155                 160
Arg Leu His Asp Gly Glu Thr Ser Leu Asn Ala Leu Arg Arg Lys Val
                165                 170                 175
Arg Gln Asp Leu Cys Ser Phe Glu Gly Asn Ala Gln Gly Ile Arg Leu
            180                 185                 190
Val His Thr Leu Met Arg Met Asn Leu Thr Trp Ala Gln Val Gly Cys
        195                 200                 205
Ile Leu Lys Tyr Thr Arg Pro Ala Trp Trp Ser Glu Glu Thr Pro Ala
    210                 215                 220
Ser His Ser Tyr Leu Met Lys Lys Pro Gly Tyr Tyr Leu Ala Glu Glu
225                 230                 235                 240
Glu Tyr Val Ala Arg Leu Arg Lys Glu Leu Asp Leu Ala Pro Tyr Asn
                245                 250                 255
Arg Phe Pro Leu Thr Trp Ile Met Glu Ala Ala Asp Asp Ile Ser Tyr
            260                 265                 270
Cys Val Ala Asp Leu Glu Asp Ala Val Glu Lys Arg Ile Phe Ser Ala
        275                 280                 285
Glu Gln Leu Tyr Gln His Leu Tyr Asp Ala Trp Gly Ser His Val Lys
    290                 295                 300
Arg Ser Arg Tyr Ser Gln Val Val Glu Asn Ala Trp Glu Lys Ser Arg
305                 310                 315                 320
Ala Asn Tyr Leu Lys Gln Ser Ala Glu Asp Gln Phe
                325                 330

<210> SEQ ID NO 22
<211> LENGTH: 7
<212> TYPE: PRT
<213> ORGANISM: Salmonella

<400> SEQUENCE: 22

His Pro Asp Glu Ala Glu Ser
1               5

-continued

<210> SEQ ID NO 23
<211> LENGTH: 7
<212> TYPE: PRT
<213> ORGANISM: Klebsiella

<400> SEQUENCE: 23

Ala Pro Gly Asp Ala Leu Gly
1               5

<210> SEQ ID NO 24
<211> LENGTH: 7
<212> TYPE: PRT
<213> ORGANISM: Yersinia

<400> SEQUENCE: 24

Asp Pro Asn Gly Gly Gly Ala
1               5

<210> SEQ ID NO 25
<211> LENGTH: 4
<212> TYPE: PRT
<213> ORGANISM: Salmonella

<400> SEQUENCE: 25

Val Val Phe Ser
1

<210> SEQ ID NO 26
<211> LENGTH: 4
<212> TYPE: PRT
<213> ORGANISM: Escherichia

<400> SEQUENCE: 26

Ser Val Ala Ala
1

<210> SEQ ID NO 27
<211> LENGTH: 4
<212> TYPE: PRT
<213> ORGANISM: Klebsiella

<400> SEQUENCE: 27

Glu Val Gln Ala
1

<210> SEQ ID NO 28
<211> LENGTH: 4
<212> TYPE: PRT
<213> ORGANISM: Yersinia

<400> SEQUENCE: 28

Leu Val Asn Thr
1

<210> SEQ ID NO 29
<211> LENGTH: 9
<212> TYPE: PRT
<213> ORGANISM: Salmonella

<400> SEQUENCE: 29

Gln Glu Gly Glu Glu Asn Leu Asn Asp
1               5

<210> SEQ ID NO 30
<211> LENGTH: 9

```
<212> TYPE: PRT
<213> ORGANISM: Escherichia

<400> SEQUENCE: 30

Arg Asp Gly Glu Glu Pro Leu Asn Glu
 1               5

<210> SEQ ID NO 31
<211> LENGTH: 9
<212> TYPE: PRT
<213> ORGANISM: Klebsiella

<400> SEQUENCE: 31

His Asp Gly Glu Thr Ser Leu Asn Ala
 1               5

<210> SEQ ID NO 32
<211> LENGTH: 9
<212> TYPE: PRT
<213> ORGANISM: Yersinia

<400> SEQUENCE: 32

Arg Glu Gly Glu Thr Glu Leu Asn Ile
 1               5

<210> SEQ ID NO 33
<211> LENGTH: 7
<212> TYPE: PRT
<213> ORGANISM: Salmonella

<400> SEQUENCE: 33

Arg Ser Arg Ile Pro Ile Arg
 1               5

<210> SEQ ID NO 34
<211> LENGTH: 7
<212> TYPE: PRT
<213> ORGANISM: Escherichia

<400> SEQUENCE: 34

Glu Thr Pro Glu Thr His His
 1               5

<210> SEQ ID NO 35
<211> LENGTH: 7
<212> TYPE: PRT
<213> ORGANISM: Klebsiella

<400> SEQUENCE: 35

Glu Thr Pro Ala Ser His Ser
 1               5

<210> SEQ ID NO 36
<211> LENGTH: 7
<212> TYPE: PRT
<213> ORGANISM: Yersinia

<400> SEQUENCE: 36

Asp Ile Pro Thr Ser His Asn
 1               5
```

DETECTION AND IDENTIFICATION OF ENTERIC BACTERIA

This application is a divisional application of U.S. application Ser. No. 09/991,552, filed Nov. 21, 2001, U.S. Pat. No. 6,696,254, which is incorporated herein by reference.

FIELD OF THE INVENTION

The invention relates to detection of Enterobacteriaceae and identification of the genus or genera of Enterobacteriaceae present in a test sample. In particular, the invention provides methods for detecting both nucleic acids and the encoded enzyme (deoxyguanosine triphosphate triphosphohydrolase) found only in Enterobacteriaceae. The nucleic acids and methods provided by the invention are useful for determining whether food, water and other types of samples are contaminated with enteric bacteria. Methods of the invention also permit identification of the type of enteric bacteria present in a contaminated sample.

BACKGROUND OF THE INVENTION

Food poisoning and other food borne diseases that are caused by enteropathogenic bacteria account for millions of illnesses and thousands of deaths each year in the United States (1,2). The clinical conditions that result from acute ingestion of pathogenic bacteria include diarrhea, vomiting, and dysentery (3). However, other more serious medical complications may occur, such as renal and cardiac disorders, neurological dysfunction, hemolytic uremia, and death (4). The situation in non-industrialized countries is even worse, where it is estimated that more than 10 percent of the population is chronically inflicted with food borne disease (5). Public health organizations have not only been faced with an ever increasing rate of food poisoning cases in the United States, but with newly emerging bacterial food borne diseases (6, 7). In addition to human health issues, food borne illnesses take a continued and a heavy economic toll on society by lowering economic productivity and by stretching the available resources of local and national public health organizations (8).

The bacteria responsible for these human illnesses are from the taxonomic family Enterobacteriaceae (9). The four main genera of bacteria within this family that pose a risk to human health via food borne illnesses are: *Escherichia, Salmonella, Shigella, and Yersinia*. All foodstuffs are susceptible to bacterial contamination of these bacteria. The original sources of this contamination may be from animal hosts (for example, cows, chickens, or pigs) that harbor systemic infections, from improper handling of otherwise uncontaminated foodstuffs (for example, poor worker hygiene), or from washing foodstuffs in contaminated water.

Traditional food and restaurant inspection techniques have relied upon visual inspection of foodstuffs and food preparation areas. However, foodstuffs contaminated with enteropathogenic bacteria often look, smell and taste normal. Many of these pathogens may also survive the cooking process (10, 11). When bacterial culturing is conducted, samples must be returned to a laboratory for microbiological testing. Such tests often take weeks to perform. Meanwhile, a potential health risk continues.

Studies by Quirk and Bessman (12) have revealed that a dGTPase is only detected in bacteria belonging to the family Enterobacteriaceae. However, this reference does not provide nucleic acids probes and antibodies capable of detecting Enterobacteriaceae in general and also distinguishing between the various types of Enterobacteriaceae.

It is therefore imperative to develop faster and more reliable detection methods that are sensitive and specific enough to identify not only that enteropathogenic bacterial contamination exists in food and water samples, but what type of enteropathogenic bacterial contamination is present.

SUMMARY OF THE INVENTION

According to the invention, the enzyme deoxyguanosine triphosphate triphosphohydrolase (dGTPase; E.C. 3.1.5.1) is found only in Enterobacteriaceae and detection of this enzyme is a specific indicator that Enterobacteriaceae pathogens are present in a test sample. The invention provides methods for identifying which genus or genera of Enterobacteriaceae is present in a contaminated sample, as well as antibodies and nucleic acids useful for detection of Enterobacteriaceae dGTPase. Such methods may involve immunological, enzymatic, hybridization, nucleic acid amplification and related procedures for detection and identification of Enterobacteriaceae.

The invention provides an isolated nucleic acid that includes SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. Such nucleic acids can selectively hybridize to DNA from a bacteria of the family Enterobacteriaceae.

The invention also provides an isolated nucleic acid that includes SEQ ID NO:7, SEQ ID NO:8, SEQ ID NO:9, or SEQ ID NO:10, These nucleic acids can selectively hybridize to DNA from *Escherichia coli* even in the presence of DNA from at least one other bacterial species of the family Enterobacteriaceae such as *Klebsiella, Salmonella, Shigella* or *Yersinia*.

The invention further provides an isolated nucleic acid that includes SEQ ID NO:11, SEQ ID NO:12, SEQ ID NO:13, or SEQ ID NO:14. These nucleic acids can selectively hybridize to DNA from *Salmonella typhymurium*, in the presence of DNA from *Klebsiella* or *Escherichia*.

The invention also provides an isolated nucleic acid that includes SEQ ID NO:15, SEQ ID NO:16, SEQ ID NO:17, or SEQ ID NO:18. These nucleic acids can selectively hybridize to DNA from *Klebsiella oxytoca*, in the presence of DNA from *Salmonella* or *Escherichia*.

The invention further provides a biosensor chip that includes a solid support and a nucleic acid including SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18.

The invention also provides a method of detecting the presence of enteric bacteria in a test sample that includes contacting the test sample with probe under stringent hybridizations conditions, and detecting hybridization between the probe and a nucleic acid in the test sample. Such a probe can include a nucleic acid that includes, for example, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18. Such enteric bacteria are of the family Enterobacteriaceae. This method may further include DNA amplification, for example, polymerase chain reaction.

The invention further provides a method of detecting the presence of any species of enteric bacteria in a test sample that includes contacting the test sample with probe under stringent hybridizations conditions, and detecting hybridization between the probe and a nucleic acid in the test sample. Probes useful in this method include nucleic acids with SEQ ID NO:2, SEQ ID NO:3, SEQ ID NO:4, SEQ ID NO:5, or SEQ ID NO:6. This method may further include DNA amplification, for example, polymerase chain reaction.

The invention also provides a method of detecting the presence of *Escherichia* in a test sample that includes contacting the test sample with probe under stringent hybridizations conditions, and detecting hybridization between the probe and a nucleic acid in the test sample. Such a probe may be an isolated nucleic acid that includes SEQ ID NO:7, SEQ ID NO:8, SEQ ID NO:9, or SEQ ID NO:10. These probes can selectively hybridize to DNA from *Escherichia coli* in the presence of DNA from Klebsiella, *Salmonella, Shigella* or *Yersinia*. This method may further include DNA amplification, for example, polymerase chain reaction.

The invention further provides a method of detecting the presence of *Salmonella* in a test sample that includes contacting the test sample with probe under stringent hybridizations conditions, and detecting hybridization between the probe and a nucleic acid in the test sample. Such a probe may be an isolated nucleic acid that includes SEQ ID NO:11, SEQ ID NO:12, SEQ ID NO:13, or SEQ ID NO:14. These probes can selectively hybridize to DNA from *Salmonella typhymurium* in the presence of DNA from *Klebsiella* or *Escherichia*. This method may further include DNA amplification, for example, polymerase chain reaction.

The invention also provides a method of detecting the presence of *Klebsiella* in a test sample that includes contacting the test sample with probe under stringent hybridizations conditions, and detecting hybridization between the probe and a nucleic acid in the test sample. Such a probe may be an isolated nucleic acid that includes SEQ ID NO:15, SEQ ID NO:16, SEQ ID NO:17, or SEQ ID NO:18. These probes can selectively hybridize to DNA from *Klebsiella oxytoca* in the presence of DNA from *Salmonella* or *Escherichia*. This method may further include DNA amplification, for example, polymerase chain reaction.

The invention also provides method for detecting enteric bacteria in a test sample that includes contacting a test sample with a biosensor chip that has a solid support and an antibody that can bind to dGTPase from Enterobacteriaceae, and detecting whether dGTPase is bound to the biosensor chip. Biosensor chips that include such a solid support and an antibody that can selectively bind to dGTPase from Enterobacteriaceae are also provided by the invention.

Antibodies that can bind to dGTPase from Enterobacteriaceae, include, for example, antibodies directed against a peptide having SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

DESCRIPTION OF THE DRAWINGS

FIG. 9 provides the DNA sequence of the *E. coli* dgt gene.

| Lane | Bacteria | Primer Pair | Band size (bp) |
|---|---|---|---|
| 1 | *Escherichia* + *Klebsiella* | 7 and 11 | 82 (*Escherichia*) + 213 (*Klebsiella*) |
| 2 | *Escherichia* + *Salmonella* | 7 and 8 | 82 (*Escherichia*) + 213 (*Salmonella*) |
| 3 | *Salmonella* + *Klebsiella* | 8 and 13 | 213 (*Salmonella*) + 82 (*Klebsiella*) |
| 4 | *Klebsiella* + *Escherichia* | 6 | 251 (*Escherichia*) |
| 5 | *Salmonella* + *Escherichia* | 6 | 251 (*Escherichia*) |

Primer pairs 5, 6 and 7 were designed to be specific for *Escherichia*. Primer pairs 8, 9 and 10 were designed to be specific for *Salmonella*. Primer pairs 11, 12 and 13 were designed to be specific for *Klebsiella*. Each of the primer pairs employed actually synthesized a DNA fragment of the predicted size for a particular genus of bacteria. Thus, the methods of the invention discriminate between DNA from related Enterobacteriaceae and correctly identify which bacterial genus is present in a mixed bacterial culture.

Figure 13:
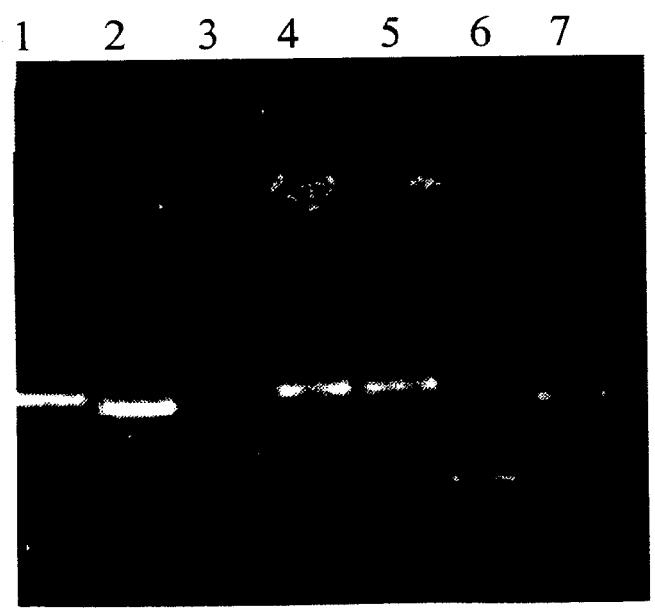

FIG. 13 illustrates that the methods of the invention can detect and identify Enterobacteriaceae within an actual meat sample (chicken). Ten μL of chicken fluid (blood) was used in a PCR reaction with the following primer sets:

| Lane No. | Primer Set | Bacterial Type Primer Designed to Detect | Observed bands (Same as Predicted) |
|---|---|---|---|
| 1 | 2 | Any enteric bacteria | 213 |
| 2 | 5 | *Escherichia* only | 213 |
| 3 | 11 | *Klebsiella* only | None |
| 4 | 8 | *Salmonella* only | 213 |
| 5 | 8 (2×) | *Salmonella* only | 213 |
| 6 | 5 + 7 | *Escherichia* only | 251 + 83 |
| 7 | 1 | Any enteric bacteria | 213 |

Twice the amount of primer set 8 was used in the reaction for lane 5 and for lane 4. The bands in lanes 6 and 7 were faint but were visibly present. These results indicate that the chicken sample was contaminated with both *Salmonella* and *Escherichia*, but not with *Klebsiella*.

DETAILED DESCRIPTION OF THE INVENTION

Deoxyguanosine triphosphate triphosphohydrolase (dGTPase) is the only enzyme that has been identified as being specifically localized in Enterobacteriaceae. No dGTPase activity is detected in extracts of eukaryotic cells, including extracts of rat and chicken livers, chicken and *Drosophila* embryos, and yeast cells. The enzyme is expressed in all of the pathogenicly important genera of the Enterobacteriaceae, but not in the *Erwinia* species. Surprisingly, the enzyme is also not expressed in the closely related *Vibrio* genus. Moreover, the dGTPase polypeptide shows little interspecies variation in expression level. This narrow taxonomic distribution of dGTPase may be utilized to identify enteropathogenic bacteria in all sorts of test samples.

Deoxyguanosine triphosphate triphosphohydrolase was discovered by Kornberg et al. (15) as a contaminant during the purification of DNA polymerase I. The enzyme was partially purified and found to catalyze the hydrolysis of deoxyguanosine triphosphate to deoxyguanosine and inorganic tripolyphosphate:

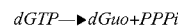

$$dGTP \rightarrow dGuo + PPPi$$

This reaction is unique among all known nucleoside triphosphatases, which either form ortho or pyrophosphate as end products. To date, dGTPase is the only known triphosphohydrolase. The dGTPase enzyme is a thermostable tetrameric protein (13, 14) and it is immunogenic (12). The enzymological and structural properties of dGTPase from the other enteric bacteria (16) are similar to dGTPase isolated from *Escherichia*.

Definitions

The term "amino acid sequence" refers to the positional arrangement and identity of amino acids in a peptide, polypeptide or protein molecule. Use of the term "amino acid sequence" is not meant to limit the amino acid sequence to the complete, native amino acid sequence of a peptide, polypeptide or protein.

The term "coding region" refers to the nucleotide sequence that codes for a protein of interest or to a functional RNA of interest, for example antisense RNA or a nontranslated RNA. The coding region of a protein is bounded on the 5' side by the nucleotide triplet "ATG" that encodes the initiator methionine and on the 3' side by one of the three triplets that specify stop codons (i.e., TAA, TAG, TGA). The coding region may be present in either a cDNA, genomic DNA or RNA form.

"Complementary" or "complementarity" are used to define the degree of base-pairing or hybridization between nucleic acids. For example, as is known to one of skill in the art, adenine (A) can form hydrogen bonds or base pair with thymine (T) and guanine (G) can form hydrogen bonds or base pair with cytosine (C). Hence, A is complementary to T and G is complementary to C. Complementarity may be complete when all bases in a double-stranded nucleic acid are base paired. Alternatively, complementarity may be "partial," in which only some of the bases in a nucleic acid are matched according to the base pairing rules. The degree of complementarity between nucleic acid strands has an effect on the efficiency and strength of hybridization between nucleic acid strands.

"Control sequences" or "regulatory sequences" are DNA sequences necessary for the expression of an operably linked coding sequence in a particular host organism. Control sequences that are suitable for prokaryotic cells include, for example, a promoter, and optionally an operator sequence, and a ribosome binding site.

"Expression" refers to the transcription and/or translation of an endogenous or exogenous gene in an organism. Expression generally refers to the transcription and stable accumulation of mRNA. Expression may also refer to the production of protein.

The term "gene" is used broadly to refer to any segment of nucleic acid associated with a biological function. The term "gene" encompasses the coding region of a protein, polypeptide, peptide or structural RNA. The term "gene-"also includes sequences up to a distance of about 2 kb on either end of a coding region. These sequences are referred to as "flanking" sequences or regions (these flanking sequences are located 5' or 3' to the non-translated sequences present on the mRNA transcript). The 5' flanking region may contain control or regulatory sequences such as promoters and enhancers or other recognition or binding sequences for proteins that control or influence the transcription of the gene. The 3' flanking region may contain sequences that direct the termination of transcription, post-transcriptional cleavage and polyadenylation as well as recognition sequences for other proteins. A protein or polypeptide encoded in a gene may be full length or any portion thereof, so that all activities or functional properties are retained, or so that only selected activities (e.g., enzymatic activity, ligand binding, signal transduction, etc.) of the full-length protein or polypeptide are retained. The protein or polypeptide may include any sequences necessary for the production of a proprotein or precursor polypeptide. The term "gene" encompasses both cDNA and genomic forms of a coding region. A genomic form of a coding region may be interrupted with non-coding sequences termed "introns." The term "native gene" refers to gene that is naturally present in the genome of an untransformed cell.

"Genome" refers to the complete genetic material that is naturally present in an organism and is transmitted from one generation to the next.

The terms "heterologous nucleic acid," or "exogenous nucleic acid" refer to a nucleic acid that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring nucleic acid. Thus, the terms refer to a nucleic acid segment that is foreign or heterologous to the cell, or normally found within the cell but in a position within the cell or genome where it is not ordinarily found.

The term "homology" refers to a degree of similarity between a nucleic acid and a reference nucleic acid or between a polypeptide and a reference polypeptide. Homology may be partial or complete. Complete homology indicates that the nucleic acid or amino acid sequences are identical. A partially homologous nucleic acid or amino acid sequence is one that is not identical to the reference nucleic acid or amino acid sequence. Hence, a partially homologous nucleic acid has one or more nucleotide differences in its sequence relative to the nucleic acid to which it is being compared. The degree of homology may be determined by sequence comparison. Alternatively, as is well understood by those skilled in the art, DNA-DNA or DNA-RNA hybridization, under various hybridization conditions, may provide an estimate of the degree of homology between nucleic acids, (see, e.g., Haines and Higgins (eds.), Nucleic Acid Hybridization, IRL Press, Oxford, U.K.).

"Hybridization" refers to the process of annealing complementary nucleic acid strands by forming hydrogen bonds between nucleotide bases on the complementary nucleic acid strands. Hybridization, and the strength of the association between the nucleic acids, is impacted by such factors as the degree of complementary between the hybridizing nucleic acids, the stringency of the conditions involved, the $T_m$ of the formed hybrid, the length of the hybridizing nucleic acids and the G:C ratio of those nucleic acids.

An "initiation site" is region surrounding the position of the first nucleotide that is part of the transcribed sequence, which is defined as position +1. All nucleotide positions of the gene are numbered by reference to the first nucleotide of the transcribed sequence, which resides within the initiation site. Downstream sequences (i.e. sequences in the 3' direction) are denominated positive, while upstream sequences (i.e. sequences in the 5' direction) are denominated negative.

An "isolated" or "purified" nucleic acid or an "isolated" or "purified" polypeptide is a nucleic acid or polypeptide that, by the hand of man, exists apart from its native environment and is therefore not a product of nature. An isolated nucleic acid or polypeptide may exist in a partially purified or substantially purified form. An isolated nucleic acid or polypeptide may also exist in a non-native environment such as, for example, a transgenic host cell.

The term "label" refers to any atom or molecule that may be used to provide a detectable (preferably quantifiable) signal, and that may be attached to a nucleic acid or protein. Labels may provide signals detectable by fluorescence, radioactivity, colorimetry, gravimetry, X-ray diffraction or absorption, magnetism, enzymatic activity, and the like.

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the reference sequence explicitly indicated.

The term "oligonucleotide" as used herein is defined as a molecule comprised of two or more deoxyribonucleotides or ribonucleotides, desirably more than three, and usually more than ten. There is no precise upper limit on the size of an oligonucleotide. However, in general, an oligonucleotide is shorter than about 250 nucleotides, more desired oligonucleotides are shorter than about 200 nucleotides and even more desired oligonucleotides are shorter than about 100 nucleotides. Most desired oligonucleotides are shorter than about 50 nucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "open reading frame" and "ORF" refer to the amino acid sequence encoded between translation initiation and termination codons of a coding sequence.

The terms "initiation codon" and "termination codon" refer to a unit of three adjacent nucleotides ('codon') in a coding sequence that specifies initiation and chain termination, respectively, of protein synthesis (mRNA translation).

"Operably linked" means that two or more nucleic acids are placed in a functional relationship with each other. For example, nucleic acids encoding a presequence or secretory leader may be operably linked to nucleic acids encoding a polypeptide, and expressed as a pre-protein that participates in the secretion of the protein; a promoter or enhancer may be operably linked to a coding sequence and effect the transcription of the sequence; or a ribosome binding site may be operably linked to a coding sequence and positioned so as to facilitate translation. Generally, "operably linked" means that the DNA sequences being linked are contiguous and, in the case of an encoded polypeptide sequence, in reading phase and generally contiguous. However, enhancers do not have to be contiguous.

The terms "protein," "peptide" and "polypeptide" are used interchangeably herein As used herein the term "stringency" is used to define the conditions of temperature, ionic strength, and the presence of other compounds such as organic solvents, under which nucleic acid hybridizations are conducted. With "high stringency" conditions, nucleic acid base pairing will occur only between nucleic acids that have a high frequency of complementary base sequences. With "weak" or "low" stringency conditions nucleic acids the frequency of complementary sequences is usually less, so that nucleic acids with differing sequences may be detected and/or isolated.

The terms "substantially similar" and "substantially homologous" refer to nucleotide and amino acid sequences that represent functional equivalents of the instant inventive sequences. For example, altered nucleotide sequences that simply reflect the degeneracy of the genetic code but nonetheless encode amino acid sequences that are identical to the inventive amino acid sequences are substantially similar to the inventive sequences. In addition, amino acid sequences that are substantially similar to the instant sequences are those wherein overall amino acid identity is sufficient to provide an active, thermally stable dGTPase. For example, amino acid sequences that are substantially similar to the sequences of the invention are those wherein the overall amino acid identity is 80% or greater, desirably 90% or greater, and more desirably 95% or greater relative to the amino acid sequences of the invention.

By "thermostable" is meant that the enzyme remains has an optimal temperature of activity at a temperature greater than about 37° C. to 42° C. Desired polymerase enzymes have an optimal temperature for activity of between about 50° C. and 75° C., more desired enzymes have an optimal temperature between 55° C. and 70° C., and most desired enzymes have an optimal temperature between 60° C. and 65° C.

The "variant"of a nucleic acid, protein, polypeptide or peptide, means that the variant nucleic acid, protein, polypeptide or peptide has a related but different sequence than a reference nucleic acid, protein, polypeptide or peptide, respectively. A variant nucleic acid differs in nucleotide sequence from a reference nucleic acid whereas a variant nucleic acid, protein, polypeptide or peptide differs in amino acid sequence from the reference nucleic acid, protein, polypeptide or peptide, respectively. A variant and reference nucleic acid, protein, polypeptide or peptide may differ in sequence by one or more substitutions, insertions, additions, deletions, fusions and truncations, which may be present in any combination. Differences may be minor (e.g. a difference of one nucleotide or amino acid) or more substantial. However, the sequence of the variant is not so different from the reference that one of skill in the art would not recognize that the variant and reference are related in structure and/or function. Generally, differences are limited so that the reference and the variant are closely similar overall and, in many regions, identical.

The term "vector" is used to refer to a nucleic acid that can transfer nucleic acid segment(s) from one cell to another. A "vector" includes, inter alia, any plasmid, cosmid, phage or nucleic acid in double or single stranded linear or circular form that may or may not be self transmissible or mobilizable, and that can transform prokaryotic or eukaryotic host either by integration into the cellular genome or by existing extrachromosomally (e.g. autonomous replicating plasmid with an origin of replication). Vectors used in bacterial systems often contain an origin of replication so that the vector may replicate independently of the bacterial chromosome. The term "expression vector" refers to a vector containing an expression cassette.

The term "wild-type" refers to a gene or gene product that has the characteristics of that gene or gene product when isolated from a naturally occurring source. A wild-type gene is the gene that is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. Naturally-occurring mutants may be isolated; these are identified by the fact that they have altered characteristics when compared to the wild-type gene or gene product.

Enterobacteriaceae dGTPase Nucleic Acids

The invention is directed to nucleic acids encoding a deoxyguanosine triphosphate triphosphohydrolase enzyme from any species of the family Enterobacteriaceae. Variant nucleic acids that encode an active deoxyguanosine triphosphate triphosphohydrolase enzyme are also contemplated by the invention. Any fragment of a nucleic acid is also encompassed by the invention so long as it can specifically hybridize to a nucleic acid encoding a deoxyguanosine triphosphate triphosphohydrolase enzyme from any species of the family Enterobacteriaceae. The nucleic acids of the invention are isolated or substantially purified nucleic acids. In particular, the isolated nucleic acids of the invention are free of nucleic acids that encode proteins and that naturally flank the present nucleic acids in the genomic DNA of the organism from which the nucleic acid is derived. Nucleic acids of the invention may be used to detect any bacterial species of the family Enterobacteriaceae. Detection may be by any procedure known to one of skill in the art, for example, any available hybridization, amplification or related procedure.

For example, the invention is directed to nucleic acids encoding all or portions of a deoxyguanosine triphosphate triphosphohydrolase enzyme from the genus *Cedecca, Citrobacter, Enterobacter, Escherichia, Hafnia, Klebsiella, Proteus, Salmonella, Serratia, Shigella,* or *Yersinia*. In one embodiment, the nucleic acid is all or a part of the nucleic acid encoding *Escherichia coli* deoxyguanosine triphosphate triphosphohydrolase, that has the following sequence

```
(SEQ ID NO:1):
ATGGCACAGATTGATTTCCGAAAAAAAATAAACTGGCATCGTCGTTACC
GTT
CACCGCAGGGCGTTAAAACCGAACATGAGATCCTGCGGATCTTCGAGAG
CG
ATCGCGGGCGTATCATCAACTCTCCGGCAATTCGTCGTCTGCAACAAAA
GA
CCCAGGTTTTTCCACTGGAGCGCAATGCCGCCGTGCGCACGCGTCTTACC
CA
CTCGATGGAAGTCCAGCAGGTGGGGCGCTACATCGCCAAAGAAATTTTA
AG
CCGTCTGAAAGAGCTTAAATTACTGGAAGCATACGGCCTGGATGAACTG
ACC
GGTCCCTTTGAAAGCATTGTTGAGATGTCATGCCTGATGCACGATATCGG
CAA
TCCGCCGTTTGGTCATTTTGGCGAAGCGGCGATAAATGACTGGTTTCGCC
AAC
GTTTGCACCCGGAAGATGCCGAAAGCCAGCCTCTGACTGACGATCGCTG
CAG
CGTGGCGGCACTACGTTTACGGGACGGGGAAGAACCGCTTAACGAGCTG
CGG
CGCAAGATTCGTCAGGACTTATGTCATTTTGAGGGGAATGCACAAGGCA
TTC
GCCTGGTGCATACATTGATGCGGATGAATCTCACCTGGGCACAGGTTGG
CGG
TATTTTAAAATATACCCGTCCGGCGTGGTGGCGTGGCGAAACGCCTGAG
ACA
CATCACTATTTAATGAAAAGCCGGGTTATTATCTTTCTGAAGAAGCCTA
TA
TTGCCCGGTTGCGTAAAGAACTTAATTTGGCGCTTTACAGTCGTTTTCCA
TTA
ACGTGGATTATGGAAGCTGCCGACGACATCTCCTATTGTGTGGCAGACC
TTG
AAGATGCGGTAGAGAAAAGAATATTTACCGTTGAGCAGCTTTATCATCA
TTT
GCACGAAGCGTGGGGCCAGCATGAGAAAGGTTCGCTCTTTTCGCTGGTG
GTT
GAAAATGCCTGGGAAAAATCACGCTCAAATAGTTTAAGCCGCAGTACGG
AA
GATCAGTTTTTTATGTATTTACGGGTAAACACCCTAAATAAACTGGTACC
CTA
CGCGGCACAACGATTTATTGATAATCTGCCTGCGATTTTCGCCGGAACGT
TTA
ATCATGCATTATTGGAAGATGCCAGCGAATGCAGCGATCTTCTTAAGCT
ATA
TAAAAATGTCGCTGTAAAACATGTGTTTAGCCATCCAGATGTCGAGCGG
CTT
GAATTGCAGGGCTATCGGGTCATTAGCGGATTATTAGAGATTTATCGTCC
TT
TATTAAGCCTGTCGTTATCAGACTTTACTGAACTGGTAGAAAAAGAACG
GGT
GAAACGTTTCCCTATTGAATCGCGCTTATTCCACAAACTCTCGACGCCGC
AT
CGGCTGGCCTATGTCGAGGCTGTCAGTAAATTACCGTCAGATTCTCCTGA
GT
TTCCGCTATGGAATATTATTACCGTTGCCGCCTGCTGCAGGATTATATC
AG
CGGTATGACCGACCTCTATGCGTGGGATGAATACCGACGTCTGATGGCC
GTA
GAACAATAA
```

Fragments and variant nucleic acids of the deoxyguanosine triphosphate triphosphohydrolase nucleic acids provided herein are also encompassed by the invention. Nucleic acid "fragments" encompassed by the invention are of two general types. First, fragment nucleic acids that do not encode a full length dGTPase but do encode a polypeptide with dGTPase activity are within the scope of the invention. Second, fragments of a nucleic acids identified herein that are useful as hybridization probes or primers but generally do not encode dGTPase activity are also included in the invention.

Fragments may be obtained or developed using the *E. coli* dGTPase nucleic acid sequence (SEQ ID NO:1), or dGTPase nucleic acid sequences from other enteric species of the family Enterobacteriaceae. Other dGTPase nucleic acid sequences may be found in the Genebank sequence repositories. Fragments used as primers may be designed to amplify any enteric dGTPase nucleic acid when the primer sequence is selected from an areas of sequence identity or conservation between enteric species. On the other hand, primer sequences may be designed to be selective for a specific genus or species of Enterobacteriaceae by selecting a sequence that is unique to that genus or species. One of skill in the art can readily design such primer sequences.

Thus, fragments of the invention may range from at least about 9 nucleotides, about 12 nucleotides, about 15 nucleotides, about 17 nucleotides, about 18 nucleotides, about 20 nucleotides, about 50 nucleotides, about 100 nucleotides or more. In general, a fragment nucleic acid of the invention can have any upper size limit so long as it is related in sequence to the nucleic acids of the invention, but is not full length.

Nucleic acid fragments of the invention can be used, for example, as hybridization probes for detecting or identifying dGTPase nucleic acids or as primers for DNA synthesis, DNA sequencing or DNA amplification of dGTPase nucleic acids. Many fragments can be obtained from SEQ ID NO:1. Examples of nucleic acid fragments of the invention include any of SEQ ID NO:1–18.

By "variants" is intended substantially similar or substantially homologous sequences. For nucleotide sequences, variants include those sequences that, because of the degeneracy of the genetic code, encode the identical amino acid sequence of a native dGTPase protein. Naturally occurring allelic variants include any Enterobacteriaceae dGTPase nucleic acid not specifically listed herein and are encompassed within the invention. Variant nucleic acids may be identified with the use of well-known molecular biology techniques, as, for example, with polymerase chain reaction (PCR) and hybridization techniques. Variant nucleic acids also include those that encode polypeptides that do not have amino acid sequences identical to that of a native dGTPase protein, but that still encode an active dGTPase.

As is known by one of skill in the art, the genetic code is "degenerate," meaning that several trinucleotide codons can encode the same amino acid. This degeneracy is apparent from Table 1.

mentary sequences thereof, as well as the sequence explicitly specified by a SEQ ID NO. Specifically, degenerate codon substitutions may be achieved by generating sequences in which the reference codon is replaced by any of the codons for the amino acid specified by the reference codon. In general, the third position of one or more selected codons can be substituted with mixed-base and/or deoxyinosine residues as disclosed by Batzer et al., Nucleic Acid Res., 19, 5081 (1991) and/or Ohtsuka et al., J. Biol. Chem., 260, 2605 (1985); Rossolini et al., Mol. Cell. Probes, 8, 91 (1994).

However, the invention is not limited to silent changes in the present nucleotide sequences but also includes variant nucleic acid sequences that alter the amino acid sequence of a polypeptide of the invention. According to the present invention, variant and reference nucleic acids of the invention may differ in the encoded amino acid sequence by one or more substitutions, additions, insertions, deletions, fusions and truncations, which may be present in any combination, so long as an active, dGTPase is encoded by the variant nucleic acid. Such variant nucleic acids will not encode exactly the same amino acid sequence as the reference nucleic acid, and are described herein as having "non-silent" sequence changes.

Variant nucleic acids with silent and non-silent changes can be defined and characterized by the degree of homology to the reference nucleic acid. Desired variant nucleic acids are "substantially homologous" to the reference nucleic acids of the invention. As recognized by one of skill in the art, such substantially similar nucleic acids can hybridize under stringent conditions with the reference nucleic acids identified by SEQ ID Nos herein. These types of substantially homologous nucleic acids are encompassed by this invention.

Generally, nucleic acid variants of the invention will have at least 50, 60, to 70% sequence identity to the reference nucleotide sequence defined herein. Desired nucleic acid

TABLE 1

| | Second Position | | | | |
|---|---|---|---|---|---|
| 1st Position | T | C | A | G | 3rd Position |
| T | TTT = Phe | TCT = Ser | TAT = Tyr | TGT = Cys | T |
| T | TTC = Phe | TCC = Ser | TAC = Tyr | TGC = Cys | C |
| T | TTA = Leu | TCA = Ser | TAA = Stop | TGA = Stop | A |
| T | TTG = Leu | TCG = Ser | TAG = Stop | TGG = Trp | G |
| C | CTT = Leu | CCT = Pro | CAT = His | CGT = Arg | T |
| C | CTC = Leu | CCC = Pro | CAC = His | CGC = Arg | C |
| C | CTA = Leu | CCA = Pro | CAA = Gln | CGA = Arg | A |
| C | CTG = Leu | CCG = Pro | CAG = Gln | CGG = Arg | G |
| A | ATT = Ile | ACT = Thr | AAT = Asn | AGT = Ser | T |
| A | ATC = Ile | ACC = Thr | AAC = Asn | AGC = Ser | C |
| A | ATA = Ile | ACA = Thr | AAA = Lys | AGA = Arg | A |
| A | ATG = Met | ACG = Thr | AAG = Lys | AGG = Arg | G |
| G | GTT = Val | GCT = Ala | GAT = Asp | GGT = Gly | T |
| G | GTC = Val | GCC = Ala | GAC = Asp | GGC = Gly | C |
| G | GTA = Val | GCA = Ala | GAA = Gln | GGA = Gly | A |
| G | GTG = Val | GCG = Ala | GAG = Gln | GGG = Gly | G |

Hence, many changes in the nucleotide sequence of the variant may be silent and may not alter the amino acid sequence encoded by the nucleic acid. Where nucleic acid sequence alterations are silent, a variant nucleic acid will encode a polypeptide with the same amino acid sequence as the reference nucleic acid.

Nucleic acid sequences of the invention also encompass variants with degenerate codon substitutions, and complevariants of the invention will have at least 71%, 72%, 73%, 74%, 75%, 76%, 77%, 78%, to 79%, sequence identity to the reference nucleotide sequence defined herein. More desired nucleic acid variants of the invention will have at least 80%, 81%, 82%, 83% or 84% sequence identity to the reference nucleotide sequence defined herein. Even more desired nucleic acids of the invention will have at least at least 85%, 86%, 87%, 88% or 89% sequence identity to the reference nucleotide sequence defined herein. Even more desired nucleic acids of the invention will have at least 90%, 91%, 92%, 93% or 94% sequence identity to the reference nucleotide sequence defined herein. Most desired nucleic acids of the invention will have at least at least 95%, 96%, 97%, to 98% sequence identity to the reference nucleotide sequence defined herein.

Variant nucleic acids can be detected and isolated by standard hybridization procedures.

Hybridization to detect or isolate such sequences is generally carried out under stringent conditions. "Stringent hybridization conditions" and "stringent hybridization wash conditions" in the context of nucleic acid hybridization experiments such as Southern and Northern hybridization are sequence dependent, and are different under different environmental parameters. Longer sequences hybridize specifically at higher temperatures. An extensive guide to the hybridization of nucleic acids is found in Tijssen, Laboratory Techniques in Biochemistry and Molecular biology-Hybridization with Nucleic Acid Probes, page 1, chapter 2 "Overview of principles of hybridization and the strategy of nucleic acid probe assays" Elsevier, New York (1993). See also, J. Sambrook et al., Molecular Cloning: A Laboratory Manual, Cold Spring Harbor Press, N.Y., pp 9.31–9.58 [1989].

The invention also provides methods for detection and isolation of variant nucleic acids encoding dGTPase activity. The methods involve hybridizing at least a portion of a nucleic acid comprising SEQ ID NOS:1 to 14 to a sample nucleic acid, thereby forming a hybridization complex; and detecting the hybridization complex. The presence of the complex correlates with the presence of a variant dGTPase nucleic acid. In general, the portion of a nucleic acid used for hybridization is at least fifteen nucleotides long. Examples of nucleic acids used in hybridization methods include nucleic acids comprising SEQ ID NOS:1–18. Hybridization is performed under hybridization conditions that are sufficiently stringent to permit detection and isolation of homologous nucleic acids.

In an alternative embodiment, nucleic acids are detected in a sample by DNA amplification using primer oligonucleotides selected from SEQ ID NOS:2–18. One such amplification method is polymerase chain reaction (PCR) described in more detail below.

While high to moderately stringent hybridization conditions are generally used to detect and isolate variant nucleic acids of the invention, nucleic acids that do not hybridize to each other under stringent conditions are still substantially identical to the reference nucleic acids if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid. Hence, as is known to one of skill in the art, high to moderately stringent hybridization conditions can be used to detect and isolate substantially homologous to the reference nucleic acid, but such substantially homologous nucleic acids can also be detected or isolated with low stringency hybridization conditions.

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions, nucleic acids that are 100% complementary can be identified.

Alternatively, stringency conditions can be adjusted to allow some mismatching in sequences so that lower degrees of similarity are detected (heterologous probing). Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl and 0.3 M trisodium citrate) at 50 to 55° C. Exemplary moderate stringency conditions include hybridization in 40 to 45% formamide, 1.0 M NaCl, 1% SDS at 37° C., and a wash in 0.5×to 1×SSC at 55 to 60° C. Exemplary high stringency conditions include hybridization in 50% formamide, 1 M NaCl, 1% SDS at 37° C., and a wash in 0.1×SSC at 60 to 65° C.

The degree of complementarity or homology of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions. For DNA-DNA hybrids, the $T_m$ may be approximated from the equation of Meinkoth and Wahl Anal. Biochem. 138:267–284 (1984):

$$T_m = 81.5° \text{ C.} + 16.6 \ (\log M) + 0.41 \ (\% \ GC) - 0.61 \ (\% \ \text{form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Very stringent conditions are selected to be equal to the $T_m$ for a particular probe.

An example of stringent hybridization conditions for hybridization of complementary nucleic acids that have more than 100 complementary residues on a filter in a Southern or Northern blot is 50% formamide with 1 mg of heparin at 42° C., with the hybridization being carried out overnight. An example of highly stringent conditions is 0.15 M NaCl at 72° C. for about 15 minutes. An example of stringent wash conditions is a 0.2×SSC wash at 65° C. for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C.

Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to detect and isolate homologous nucleic acids that are substantially identical to reference nucleic acids of the present invention: a reference nucleotide sequence desirably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., desirably in 7% sodium dodecyl sulfate (SDS), 0.5 M NaPO$_4$, 1 mM EDTA at 50° C. with washing in 0.1×SSC, 0.1% SDS at 50° C., more desirably in 7% sodium dodecyl sulfate (SDS), 0.5 M NapO$_4$, 1 mM EDTA at 50° C. with washing in 0.1×SSC, 0.1% SDS at 65° C.

In general, $T_m$ is reduced by about 1° C. for each 1% of mismatching. Thus, $T_m$, hybridization, and/or wash conditions can be adjusted to hybridize to sequences of the desired sequence identity. For example, if sequences with >90% identity are sought, the $T_m$ can be decreased 10° C. Generally, stringent conditions are selected to be about 5° C. or more lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

If the desired degree of mismatching results in a $T_m$ of less than 45° C. (aqueous solution) or 32° C. (formamide solution), it is desirable to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, N.Y. ); and Ausubel et al., eds. (1995) Current Protocols in Molecular Biology, Chapter 2 (Greene Publishing and Wiley—Interscience, New York). See also, Sambrook et al. (1989) Molecular Cloning: A Laboratory Manual (2d ed., Cold Spring Harbor Laboratory Press, Plainview, N.Y.). Using these references and the teachings herein on the relationship between $T_m$, mismatch, and hybridization and wash conditions, those of ordinary skill can generate variants of the present dGTPase nucleic acids.

Computer analyses can also be utilized for comparison of sequences to determine sequence identity. Such analyses include, but are not limited to: CLUSTAL in the PC/Gene program (available from Intelligenetics, Mountain View, Calif.); the ALIGN program (Version 2.0) and GAP, BEST-FIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is described by Higgins et al. Gene 73:237 244 (1988); Higgins et al. CABIOS 5:151–153 (1989); Corpet et al. Nucleic Acids Res. 16:10881–90 (1988); Huang et al. CABIOS 8:155–65 (1992); and Pearson et al. Meth. Mol. Biol. 24:307–331(1994).

The BLAST programs are described by Altschul et al., J. Mol. Biol. 215:403 (1990). To obtain gapped alignments for comparison purposes, Gapped BLAST (in BLAST 2.0) can be utilized as described in Altschul et al. Nucleic Acids Res. 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) may be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA, 89, 10915 (1989)). See http://www.ncbi.nlm.nih.gov. Alignment may also be performed manually by inspection.

For purposes of the present invention, comparison of nucleotide sequences for determination of percent sequence identity to the dGTPase sequences disclosed herein is desirably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the desired program.

Enterobacteriaceae dGTPase Protein

The invention provides isolated dGTPase polypeptides from any species of Enterobacteriaceae, as well as fragments thereof and variant dGTPase polypeptides that retain dGTPase activity. In one embodiment, the invention provides a polypeptide of SEQ ID NO:19, that is a wild type *Escherichia coli* dGTPase polypeptide:

```
  1  MAQIDFRKKI  NWHRRYRSPQ  GVKTEHEILR  IFESDRGRII

NSPAIRRLQQ

51  KTQVFPLERN  AAVRTRLTHS  MEVQQVGRYI  AKEILSRLKS

LNTELTGPFE

101  SIVEYACLMH  DIAIRRLVIL  AKRTINDWFG  QRLHPEDAES

QPLTDRCSVA

151  ALRLRTGKNR  LTSCGARFVR  TYVILRGMHK  HSPGAYIDAD

ESHLGTGWRY
```

-continued

```
201 FKIYPSGVVA CETPETHHYL MKKPGYYLSE EAYIARLRKE

LNLALYSRFP

251 LTWIMEAADD ISYCVADLED AVEKRIFTVE QLYHHLHEAW

GQHEKGSLFS

301 LVVENAWEKS RSNSLSRSTE DQFFMYLRVN TLNKLVPYAA

QRFIDNLPAI

351 FAGRFNHALL EDASECSDLL KLYKNVAVKH VFSHPDVERL

ELQGYRVISG

401 LLEIYRPLLS LSLSDFTELV EKERVKRFPI ESRLFHKLST

PHRLAYVEAV

451 SKLPSDSPEF PLWEYYYRCR LLQDYISGMT DLYAWDEYRR

LMAVEQ
```

In another embodiment, the invention provides a polypeptide of SEQ ID NO:20, that is a wild type *Salmonella typhimurium* dGTPase polypeptide:

```
  1 MASIDFRNKI NWHRRYRSPQ GVKTEHEILR IFESDRGRLI

NSPAIRRLQQ

51 KTQVFPLERN AAVRTRLTHS MEVQQVGRYI AKEILSRLKE

QDRLEEYGLD

101 ALTGPFESIV EMACLMHDIG NPPFGHFGEA AINDWFRQRL

HPEDAESQPL

151 THDRCVVFSL RLQKYVRDIC HLKACTREFV CTIRSCGGIL

TWAAVRPNFK

201 NIPVPACWPR GRSRIPIRYL MKKPRYYLSE EKYIARLRKE

LQLRPYSRFP

251 LTWIMEAADD ISYCVADLED AVEKRIFSVE QLYHHLYHAW

CHHEKDSLFE

301 LVVGNAWEKS RANTLSRSTE DQFFMYLRVN TLNKLVPYAQ

RFIDNLPQIF

351 AGTFNQALLE DASGFSRLLE LYKNVAVEHV FSHPDVEQLE

LQGYRVISGL

401 LDIYQPLLSL SLNDFRELVE KERLKRFPIE SRLFQKLSTR

HRLAYVEVVS

451 KLPTDSAEYP VLEYYYRCRL IQDYISGMTD LYAWDEYRRL

MAVEQ
```

In another embodiment, the invention provides a polypeptide of SEQ ID NO:21, that is a wild type *Klebsiella oxytoca* dGTPase polypeptide:

```
  1 MAKIDFRNKI NWRRRFRSPP RVETERDILR IFESDRGRIV

NSPAIRRLQQ
```

-continued

```
 51 KTQVFPLERN GRVRTRLTHS LEVQQVGRYI AKEVLSRLKE

LRLLEEYGLE

101 ELTGPFESVV EMACLMHDIG NPPFGHFGEA AINDWFRQRL

APGDALGQPL

151 TDDRCEVQAL RLHDGETSLN ALRRKVRQDL CSFEGNAQGI

RLVHTLMRMN

201 LTWAQVGCIL KYTRPAWWSE ETPASHSYLM KKPGYYLAEE

EYVARLRKEL

251 DLAPYNRFPL TWIMEAADDI SYCVADLEDA VEKRIFSAEQ

LYQHLYDAWG

301 SHVKRSRYSQ VVENAWEKSR ANYLKQSAED QF
```

The invention further provides peptides that are uniquely found in certain Enterobacteriaceae bacterial species. These peptides are listed below in Table 2.

TABLE 2

| Species | Positions | Sequence | SEQ ID NO: |
|---------|-----------|----------|------------|
| Salmonella | 141–147 | HPDEAES | 22 |
| Escherichia | 141–147 | HPDEAES | 22 |
| Klebsiella | 141–147 | APGDALG | 23 |
| Yersinia | 141–147 | DPNGGGA | 24 |
| Salmonella | 156–159 | VVFS | 25 |
| Escherichia | 156–159 | SVAA | 26 |
| Klebsiella | 156–159 | EVQA | 27 |
| Yersinia | 156–159 | LVNT | 28 |
| Salmonella | 163–171 | QEGEENLND | 29 |
| Escherichia | 163–171 | RDGEEPLNE | 30 |
| Klebsiella | 163–171 | HDGETSLNA | 31 |
| Yersinia | 163–171 | REGETELNI | 32 |
| Salmonella | 221–227 | RSRIPIR | 33 |
| Escherichia | 221–227 | ETPETHH | 34 |
| Klebsiella | 221–227 | ETPASHS | 35 |
| Yersinia | 221–227 | DIPTSHN | 36 |

The polypeptides and peptides of the invention are isolated or substantially purified polypeptides. In particular, the isolated polypeptides of the invention are substantially free of other proteins normally present in Enterobacteriaceae bacteria. Preparations and compositions of the present polypeptides are substantially free of cellular material. For example, such preparations and compositions have less than about 30%, 20%, 10%, or 5%, (by dry weight) of contaminating protein.

By "variant" polypeptide is intended a polypeptide from an Enterobacteriaceae bacterial species other than *E. coli* or a polypeptide derived from any Enterobacteriaceae dGTPase by deletion or addition of one or more amino acids to the N-terminal and/or C-terminal end of the dGTPase polypeptide; deletion or addition of one or more amino acids at one or more sites within the dGTPase polypeptide; or substitution of one or more amino acids at one or more sites within the dGTPase polypeptide. Thus, the polypeptides of the invention may be altered in various ways including amino acid substitutions, deletions, truncations, and insertions.

Such variant polypeptides may result, for example, from genetic polymorphism or from human manipulation. Methods for such manipulations are generally known in the art. For example, amino acid sequence variants of the polypeptides may be prepared by mutations in the DNA. Methods for mutagenesis and nucleotide sequence alterations are well known in the art. See, for example, Kunkel, Proc. Natl. Acad. Sci. USA, 82, 488 (1985); Kunkel et al., methods in Enzymol., 154, 367 (1987); U.S. Pat. No. 4,873,192; Walker and Gaastra, eds., Techniques in Molecular biology, MacMillan Publishing Company, New York (1983) and the references cited therein. Guidance as to appropriate amino acid substitutions that do not affect biological activity of the protein of interest may be found in the model of Dayhoff et al., Atlas of Protein Sequence and Structure, Natl. Biomed. Res. Found., Washington, D.C. (1978), herein incorporated by reference.

The variants of the isolated polypeptides of the invention have identity with at least about 60% of the amino acid positions of SEQ ID NO:19–36. In a desired embodiment, polypeptide variants have identity with at least about 70% of the amino acid positions of SEQ ID NO:19–36. More desired polypeptide variants have at least about have identity with at least about 80% of the amino acid positions of SEQ ID NO:19–36. Even more desired polypeptide variants have at least about have identity with at least about 90% of the amino acid positions of SEQ ID NO:19–36. Most desired variant polypeptide variants have at least about have identity with at least about 95% of the amino acid positions of SEQ ID NO:19–36. Especially desired variant polypeptide variants have at least about have identity with at least about 95% of the amino acid positions of SEQ ID NO:20–36. Such variants can have dGTPase activity and/or are immunologically reactive with antibodies raised against the present dGTPase polypeptides and peptides.

Amino acid residues of the isolated polypeptides and polypeptide variants may be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 3.

TABLE 3

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |

TABLE 3-continued

| Amino Acid | One-Letter Symbol | Common Abbreviation |
|---|---|---|
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | Abbreviation? |
| 3-Benzothienyl alanine | | Abbreviation? |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| ρ-Aminophenylalanine | | Phe(pNH2) |
| N-methylvaline | | MeVal |
| Homocysteine | | hCys |
| Homoserine | | hSer |
| ε-Amino hexanoic acid | | Aha |
| δ-Amino valeric acid | | Ava |
| 2,3-Diaminobutyric acid | | Dab |

Polypeptide variants that are encompassed within the scope of the invention may have one or more amino acids substituted with an amino acid of similar chemical and/or physical properties, so long as these variant polypeptides retain dGTPase activity and/or remain immunologically reactive with antibodies raised against dGTPase polypeptides having SEQ ID NO:19–36.

Amino acids that are substitutable for each other generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but that has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classification are not absolute. Several amino acids exhibit more than one characteristic property, and can therefore be included in more than one category. For example, tyrosine has both an aromatic ring and a polar hydroxyl group. Thus, tyrosine has dual properties and may be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids that are not genetically encoded and that can be present, or substituted for an amino acid, in the variant polypeptides of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); .beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH2)); N-methyl valine (MeVal); homocysteine (hCys) and homoserine (hSer). These amino acids also fall into the categories defined above.

The classifications of the above-described genetically encoded and non-encoded amino acids are summarized in Table 4, below. It is to be understood that Table 4 is for illustrative purposes only and does not purport to be an exhaustive list of amino acid residues that may comprise the variant polypeptides described herein. Other amino acid residues that are useful for making the peptides and peptide analogues described herein may be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 4

| Classification | Genetically Encoded | Genetically Non-Encoded |
|---|---|---|
| Hydrophobic | F, L, I, V | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | S, K | Cit, hCys |
| Acidic | D, E | |
| Basic | H, K, R | Dpr, Orn, hArg, Phe(p-NH2), DBU, A2 BU |
| Polar | Q, N, S, T, Y | Cit, AcLys, MSO, hSer |
| Cysteine-Like | C | Pen, hCys, β-methyl Cys |

Polypeptides of the invention can have any amino acid substituted by any similarly classified amino acid to create a variant peptide, so long as the peptide variant retains dGTPase activity and/or is immunologically reactive with antibodies raised against dGTPase polypeptides having any one of SEQ ID NO:19–36.

Thus, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. One skilled in the art can readily evaluate the thermal stability and dGTPase activity of the polypeptides and variant polypeptides of the invention by routine screening assays.

The activity of dGTPases and variant dGTPase polypeptides can be assessed by any procedure known to one of skill in the art. For example, the method described by Seto et al.

(13) can be used, which involves measuring the hydrolysis of dGTP to PPPi. In general, a mixture is prepared with dGTP, MgCl2 and the dGTPase polypeptide to be tested. After incubation at 37° C., the reaction is terminated, the mixture is centrifuged, and an aliquot of the supernatant acidified, and boiled. The acidification and boiling hydrolyzes the tripolyphosphate to orthophosphate. The total orthophosphate concentration can then be determined by any available method. For example, orthophosphate can be detected colorimetrically by the addition of an ascorbate-molybdate solution, which gives rise to a product detectable at 780 nm.

Preparation of dGTPase Polypeptides

Methods are readily available to those skilled in the art for constructing expression cassettes and vectors containing a nucleic acid of the invention that encodes a dGTPase polypeptide with appropriate transcriptional/translational control signals. For example, in vitro recombinant DNA techniques, synthetic techniques and in vivo recombination/genetic techniques can be used to make expression cassettes and vectors. See, for example, the techniques described in Sambrook et al., Molecular Cloning: A Laboratory Manual, Cold Spring Harbor Laboratory Press (2d ed.) (1989) and Sambrook et al., Molecular Cloning: A Laboratory Manual, Cold Spring Harbor Laboratory Press (3d ed.) (2001).

Generally, an expression cassette is in the form of chimeric DNA that can be part of an expression vector comprising a plasmid DNA and the nucleic acids encoding the polypeptide(s) of interest, flanked by control sequences that promote the expression, or stop the expression, of the DNA segment encoding the polypeptide. Aside from nucleic acids that serve as expression cassettes for dGTPase polypeptides, a portion of the expression vector may be untranscribed, serving a regulatory, replication or a structural function. Additional transcribed portions of the expression vector can include selectable markers, vector-specific replication functions, and the like. Other elements functional in the host cells, such as enhancers, polyadenylation sequences and the like, may also be a part of the expression vector. Such elements can provide improved expression of the dGTPase nucleic acids by affecting transcription, mRNA stability, or another factor influencing the performance of the expression vector in a host cell.

Thus, depending on the host/vector system utilized, any of a number of suitable transcription and translation elements including constitutive and inducible promoters, transcription enhancer elements, transcription terminators, and the like can be used in the expression vector (see, e.g., Bitter et al., 1987; WO 97/11761 and WO 96/06167). For example, when cloning in bacterial systems, inducible promoters such as pL of bacteriophage λ; plac, ptrup, ptac (ptrp-lac hybrid promoter) and the like may be used. Promoters produced by recombinant DNA or synthetic techniques can also be used to provide for controlled and high level transcription of the inserted coding sequence.

The expression cassette may encode other peptides. For example, an expression cassette comprising an isolated nucleic acid of the invention can be fused in-frame to another nucleic acid encoding a peptide, polypeptide or protein, which is expressed as a fusion protein containing at least a segment of a dGTPase polypeptide. In this embodiment, the isolated nucleic acid includes a first DNA segment encoding an immunogenic dGTPase peptide and a second DNA segment encoding a carrier protein. The carrier protein can facilitate purification of the resulting fusion polypeptide and/or can help activate T helper cells. The carrier protein desirably possesses low immunoreactivity.

The expression cassette to be introduced into the cells can also contain either a selectable marker gene or a reporter gene, or both, to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic-resistance genes.

Reporter genes are used for identifying transformed cells and for evaluating the functionality of regulatory sequences. Desirable reporter genes encode polypeptides that can be easily assayed. Many such reporter genes are known in the art. In general, a reporter gene is a gene that is not present in or expressed by the recipient organism or tissue and that encodes a polypeptide whose expression is manifested by some easily detectable property, e.g., enzymatic activity. Desired genes include the chloramphenicol acetyl transferase gene (cat) from Tn9 of *E. coli*, the beta-glucuronidase gene (gus) of the uidA locus of *E. coli*, and the luciferase gene (luc) from firefly *Photinus pyralis*. Expression of the reporter gene is assayed at a suitable time after the DNA has been introduced into the recipient cells.

Expression vectors can be readily introduced into host cells, e.g., mammalian, plant, bacterial, yeast or insect cells by transfection with an expression cassette by any procedure useful for the introduction into a particular cell, e.g., calcium phosphate precipitation, lipofection, microinjection, electroporation, and the like, to yield a transformed cell, so that the peptide, e.g., fusion protein, of the present invention is expressed by the host cell.

General methods for isolating and purifying a recombinantly expressed protein from a host cell are available to those in the art. For example, the culture medium or lysate can be centrifuged to remove particulate cell debris. The insoluble and soluble polypeptide fractions are then separated. The peptide of the invention may then be purified from the soluble fraction or the insoluble fraction, i.e., refractile bodies (see, for example, U.S. Pat. No. 4,518,526, the disclosure of which is incorporated by reference herein). The peptide can be purified according to standard procedures of the art, including ammonium sulfate precipitation, affinity columns, column chromatography, gel electrophoresis and the like (see, generally, Scopes, 1982; Deutscher 1990). Substantially pure compositions of at least about 90 to 95% homogeneity are desirable, and compositions of 98 to 99% or more homogeneity are more desirable. Examples of the isolation and purification of recombinant polypeptides and proteins are given in Sambrook et al., cited supra.

For example, the dGTPase polypeptides of the invention can be prepared from enteric or recombinant bacterial cells collected by centrifugation. After washing in buffer, the cells can be disrupted by sonication and the sonicate clarified by centrifugation. Because the dGTPases of the invention are thermostable, the supernatant from the sonication step can be heated at about 60° C. and precipitated proteins removed by centrifugation. The supernatant containing dGTPase polypeptides can be further purified using a DEAE Sepharose column with elution using a gradient of KCl. Further purification can be achieved using a single-stranded DNA cellulose column. After applying the semi-purified dGTPase preparation and washing off impurities with a KCl solution, active dGTPase can be eluted from the column with using higher concentration of KCl. The dGTPase enzyme can also be concentrated via pressure filtration and dialyzed into new buffers needed.

The activity of dGTPases can be assessed by any procedure known to one of skill in the art. For example, the method described by Seto et al. (13) can be used that involves measuring the hydrolysis of dGTP to PPPi. In general, a mixture is prepared with dGTP, $MgCl_2$ and the dGTPase to be tested. After incubation at 37° C., the reaction was terminated, the mixture was centrifuged, and an aliquot of the supernatant acidified, and boiled. The acidification and boiling hydrolyzes the tripolyphosphate to orthophosphate. The total orthophosphate concentration can then be determined by any available method. For example, orthophosphate can be detected colorimetrically by the addition of an ascorbate-molybdate solution, which gives rise to a product detectable at 780 nm.

Antibodies

The present invention also provides antibodies directed against any Enterobacteriaceae dGTPase including, for example, any one of SEQ ID NO:19–36. More desirable antibody preparations are directed against a peptide or polypeptide having any one of any one of SEQ ID NO:20–36. Immunologically active fragments of the present antibodies are also within the scope of the present invention, e.g., F(ab) fragments.

Antibodies may be prepared by any of a variety of techniques known to those of ordinary skill in the art. See, e.g., Harlow and Lane, Antibodies: A Laboratory Manual, Cold Spring Harbor Laboratory, 1988. In one such technique, an immunogen comprising an entire dGTPase polypeptide or an antigenic portion of a dGTPase polypeptide is injected into any of a wide variety of mammals (e.g., birds, mice, rats, rabbits, sheep and goats). The immunogen can be bound to a carrier peptide and/or emulsified using a biologically suitable emulsifying agent, such as Freund's incomplete adjuvant. The immunogen is injected into the animal host, desirably according to a predetermined schedule incorporating one or more booster immunizations.

After immunization, the animals are bled periodically, blood cells are removed and the serum (antiserum) can be used as a source of polyclonal antibodies. Polyclonal antibodies can be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, Eur. J. Immunol. 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells may then be immortalized by fusion with a myeloma cell fusion partner, desirably one that is syngeneic with the immunized animal, using one of a variety of techniques well known in the art.

Monoclonal antibodies may be isolated from the supernatants of the resulting hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood of that host.

Monoclonal antibodies offer certain advantages in comparison to polyclonal antibodies. In particular, monoclonal antibodies are highly specific and sensitive and relatively "pure" immunochemically. A monoclonal antibody also may be subjected to the techniques of recombinant DNA technology to produce other derivative antibodies, humanized or chimeric molecules or antibody fragments that retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see, for example, EP 184187A and EP 2188638A, herein incorporated by reference).

Biosensors

The antibodies or nucleic acids of the invention can be absorbed or attached to a solid support or substrate to facilitate detection of Enterobacteriaceae. Such articles are useful for identifying which genus or species of bacteria is present within a test sample. Solid supports or substrates may be biosensors or a dipsticks. Antibodies and nucleic acids are bound to the support in an amount and manner that allows binding of dGTPase polypeptides or complementary nucleic acids. The amount of the antibodies and nucleic acids used relative to a given substrate depends upon the particular antibody or nucleic acid being used, the particular substrate, and the antibody-polypeptide binding or nucleic acid hybridization efficiency.

The antibodies and nucleic acids of the invention may be bound to the substrate in any suitable manner. Covalent, noncovalent, or ionic binding may be used. Covalent bonding can be accomplished by attaching the antibodies or nucleic acids to reactive groups on the substrate directly or through a linking moiety.

The solid support may be any insoluble material to which the antibodies or nucleic acids can be bound and that may be conveniently used in the assay of the invention. The biosensor or solid support can be formed from a rigid support. Alternatively, the antibodies or nucleic acids may be bound to any porous or liquid permeable material, such as a fibrous (paper, felt, nitrocellulose and the like) strip or sheet, or a screen or net, or any matrix material that one of skill in the art can conveniently use in an assay for Enterobacteriaceae. Such solid supports include permeable and semipermeable membranes, quartz, glass beads, plastic beads, latex beads, plastic microtiter wells or tubes, agarose or dextran particles, sepharose, and diatomaceous earth. The substrate of the solid support may be functionalized glass, quartz, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those skilled in the art upon review of this disclosure. In a desirable embodiment the substrate is quartz, flat glass, silica or silicon wafer.

The surface of the solid substrate or chip can be coated with other materials, for example, polymers, plastics, resins, polysaccharides, carboxymethyldextran, silica or silica-based materials, carbon, metals, inorganic glasses, membranes, or any of the above-listed substrate materials. In one embodiment, the substrate or chip is a silicon wafer coated with one or more metals and then coated with a polysaccharide. For example, the substrate or chip can be coated with gold, silver, chromium and/or combinations or layers of metal, such as chromium and gold. Metal depositions can be carried out by electro-deposition, by use of a sputtering device or by use of a cryo-pumped evaporator at reduced air pressure. The metal coat can then be coated with a polysaccharide such as carboxymethyldextran.

Distinct types of antibodies and nucleic acids can be arrayed on a substrate or chip in addressable rows and columns. Procedures and devices are available to read information from such arrays of rows and columns. For easy and/or automated detection, the size of the separate antibody or nucleic acid loci is uniform. For example, each locus can be a square, rectangle or other simple geometric shape with an area of about one square micron to about 500 square microns. The size of the loci can vary depending on the specificity and affinity of the adsorbed or immobilized antibody, the density of the antibody at a given locus and the strength of the signal or the sensitivity of the detection procedure. Similarly, the size of the loci can vary with the degree of complementarity between the nucleic acid probe and target, the density of the probe molecules on the substrate and the sensitivity of the detection procedure.

Antibodies and nucleic acid probes may be absorbed, attached or immobilized on the substrate or chip by any available procedure known to one of skill in the art. The selected antibody or probe may be immobilized to the substrate, support or chip by adsorption or covalent attachment. If covalent coupling is chosen, a wide variety of known methods can be employed including derivatizing the support with the following functional groups: benzoyl azide, bromoacetamide, azidoaryl, aldehyde, isothiocyanate, diazonium salt, acid chloride, active ester, iminocarbonate, hydrazide, epoxy, and amine.

In a desirable embodiment, a biosensor with attached nucleic acid or anti-dGTPase antibodies is used with detection by surface plasmon resonance (SPR). The selected antibodies or nucleic acids are coupled to the surface of a gold coated quartz substrate. Test samples which may contain dGTPase polypeptides or nucleic acids are applied and allowed to flow over the surface of the biosensor. After rinsing the surface of the biosensor, bound dGTPase polypeptides or nucleic acids are detected by measuring the developing surface plasmon.

Although the methods of the invention can be used with any detection strategy, including, for example, lateral flow assays, PCR, ELISA, and enzymatic detection, the surface plasmon resonance technique offers higher detection sensitivity and speed than any other detection strategy (32–34). The biosensor-surface plasmon resonance technique can detect nanogram quantities of the dGTPase enzyme. Such detection sensitivity is an order of magnitude better than published PCR based detection methods and results can be obtained in about half the time (29–31).

In one embodiment, a CM5 unmodified biosensor chip from BiaCore, Inc. is used. This chip is an approximate 1 cm square quartz crystal that was coated with a thin gold layer. Attached to the gold layer was a tether of carboxymethyldextran. The terminal carboxyl groups of the carboxymethyldextran are easily modified in order to create reactive groups for protein or nucleic acid coupling. For example, the chip surface can be reacted with a solution of 100 mM N-ethyl-N'(dimethylaminopropyl) carbodiimide hydrochloride (EDC) and 50 mM N-hydroxysuccinimide (NHS) in 25 mM sodium bicarbonate (pH 8.5) for 5 minutes, followed by a brief rinse with 100 mM borate (pH 8.5). This provides an activated CM5 chip. The activated chip can then be incubated in 80 mM 2-(2-pyridinyldithio)ethaneamine (PDEA), 0.1 M borate (pH 8.5) for four minutes, followed by a brief rinse in 0.1 M borate (pH 8.5). The chip is then placed in contact with a solution of purified antibodies or nucleic acids. Finally, all reactive disulfides are deactivated, and non-covalently bound protein or nucleic acids are removed by soaking the chip surface in a cysteine solution containing salt (e.g. NaCl).

Hence, the present invention provides a biosensor that includes a solid substrate with an antibody or a nucleic acid adsorbed or covalently attached thereto. The solid substrate of the biosensor can have a pattern or array of different antibody or nucleic acid probe types. The surface of the biosensor can also have different antibody or nucleic acid probe concentrations adsorbed or covalently attached thereto. Such an array can have a density of at least about 10 antibody or nucleic acid probe loci per square cm, and up to about one million antibody or nucleic acid probe loci per square centimeter.

Any surface plasmon resonance device can be used for detection of bound antigen or nucleic acids. In one embodiment, a Texas Instruments portable SPR instrument (TISPR-1) is desirable because the entire detection procedure can be performed in the field, by relatively untrained personnel, using a variety of sensor chips that contain different anti-dGTPase antibodies or nucleic acids depending on the needs of the inspector or the consumer.

dGTPase Detection Methods

The dGTPase nucleic acids and/or the dGTPase enzymes of the invention can serve as a key basis for a method of detecting Enterobacteriaceae and for a diagnostic device to facilitate performing that method. In general, any procedure known to one of skill in the art for detecting a nucleic acid or protein can be used for detecting the dGTPase polypeptides and nucleic acids described herein. For example, any molecular biology technique can be used, including immunoassay, hybridization or PCR procedures. Biophysical detection procedures can be used coupled with such procedures, or used separately as dictated by one of skill in the, for example, procedures such as surface plasmon resonance, fluorescence, lateral flow procedures. These procedures produce a robust and useful means of detecting and identifying enteric bacterial contamination in test samples.

In one embodiment, the invention provides a method for detecting Enterobacteriaceae in a test sample that involves contacting an antibody capable of binding to a dGTPase polypeptide isolated from an Enterobacteriaceae bacteria with a test sample and detecting whether a dGTPase polypeptide from the test sample has bound to the antibody. Such a detection method is conducted at a temperature and under conditions sufficient for antigen-antibody interaction.

In another embodiment, the invention provides a method for detecting Enterobacteriaceae in a test sample that involves contacting a nucleic acid probe with the test sample under stringent hybridization conditions and detecting whether the nucleic acid probe has hybridized with a dGTPase nucleic acid in the test sample. Nucleic acids useful as probes for Enterobacteriaceae include any of the nucleic acids provided by the invention, for example, nucleic acids having SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18.

In one embodiment, the invention provides probes that can detect the presence of any species of enteric bacteria (Enterobacteriaceae) in a test sample, for example, SEQ ID NO:2, SEQ ID NO:3, SEQ ID NO:4, SEQ ID NO:5, or SEQ ID NO:6. However, the invention also provides probes and methods for detecting one or more selected genus of bacteria within the family of Enterobacteriaceae. Such probes and methods are useful for identifying which species of Enterobacteriaceae is present in a test sample. Thus, for example, probes made from nucleic acids having SEQ ID NO:7, SEQ ID NO:8, SEQ ID NO:9, or SEQ ID NO:10 can selectively hybridize to DNA from *Escherichia coli* in the presence of DNA from *Klebsiella, Salmonella, Shigella* or *Yersinia*. Probes made from nucleic acids having SEQ ID NO:11, SEQ ID NO:12, SEQ ID NO:13, or SEQ ID NO:14 can selectively hybridize to DNA from *Salmonella typhymurium*, in the presence of DNA from *Klebsiella* or *Escherichia*. Probes made from nucleic acids having SEQ ID NO:15, SEQ ID NO:16, SEQ ID NO:17, or SEQ ID NO:18 can selectively hybridize to DNA from *Klebsiella oxytoca* in the presence of DNA from *Salmonella* or *Escherichia*.

The detection methods of the invention are not limited to hybridization and PCR methods but also include any immunological or immunoassay method that one of skill in the art can adapt for use with the present antibodies and dGTPase polypeptides. For example, the invention includes a method for detecting enteric bacteria in a test sample that includes, contacting a test sample with a biosensor chip that comprises a solid support and an antibody that can bind to dGTPase from Enterobacteriaceae; and detecting whether dGTPase is bound to the biosensor chip.

Test samples which can be used in the present hybridization, immunological and PCR procedures include, for example, physiological fluids and samples from humans or animals, food samples, water, soil, as well as samples taken from work areas, counter-tops, shelving, storage areas for food, animal or poultry pens, or from the skin, hair, or surface of an animal. Such applications include human disease state testing.

Antibodies may be used in diagnostic tests to detect the presence of Enterobacteriaceae and species or genuses thereof, by binding to dGTPase antigens. Any antibody-antigen procedure known by to one of skill in the art can be adapted for use with the present antibodies and dGTPase polypeptides. Immunoassays contemplated by the invention desirably involve use of the present biosensors, but other antibody preparations and procedures can also be used, such as those involving radioimmunoassay, ELISA, or an immunofluorescence assay. Thus, for example, immunoassays that are suitable for detecting an antigen such as the dGTPase polypeptides of the invention include those described in U.S. Pat. Nos. 3,791,932; 3,817837; 3,839,153; 3,850,752; 3,850,578; 3,853,987; 3,867,517; 3,879,262; 3,901,654; 3,935,074; 3,984,533; 3,996,345; 4,034,074; and 4,098,876.

In one embodiment, the invention provides a method for detecting Enterobacteriaceae by contacting antibodies of the invention with the sample for a period of time and under conditions sufficient for antibodies to bind to the dGTPase polypeptide so as to form a binary complex between at least a portion of the antibody and a portion of the dGTPase polypeptide. Such times, conditions and reaction media can be readily determined by persons skilled in the art. For example, to test for the presence of Enterobacteriaceae bacterial cells, a portion of the sample may be cultured and another portion may be lysed to yield an extract that comprises cellular proteins. The anti-dGTPase antibodies are then incubated with the protein extract, e.g., using the biosensor chips provided herein, or a Western blot, or any other preparation of antibodies provided herein that is capable of forming a detectable complex with an Enterobacteriaceae dGTPase. The presence or amount of the complex is then determined or detected, e.g., through determination or detection of a label.

Optionally, a blocking agent is employed prior to the addition of the antibodies, or when the antibodies are added to the test sample, or after rinsing away any un-bound antibodies, to block any non-specific binding sites with a protein such as bovine serum albumin (BSA), if desired. A second reagent, e.g., an antibody that binds to the Fc of the primary antibody, can then be added. After this second incubation, any unreacted antibody is removed as by rinsing. Hence, a ternary complex of antigen, primary antibody and secondary antibody is formed. The second antibody may be labeled to facilitate detection of the ternary complex. Such a label can be, for example, a fluorescent dye. Alternatively, the primary or secondary antibody may bind a detectable label.

Detection or measuring the formation of such complexes can also include a reagent capable of binding to the complexes formed by the dGTPase polypeptides and antibodies, and/or a label, reporter molecule or other detectable moiety. Such a reagent may be an antibody of the invention or an antibody that can bind to an antibody of the invention, that is conjugated to a detectable label, or reporter molecule.

The use of whole, intact antibodies is not necessary for many immunoassays. Instead, the antigen binding site alone may be used or single chain recombinant antibodies can be used. Examples of such antibody combining sites are those known in the art as Fab and F(ab')$_2$ antibody portions that are prepared by proteolysis using papain and pepsin, respectively, as is well known in the art.

In one embodiment, the dGTPase nucleic acids of the invention are used in procedures involving DNA amplification. Any such DNA amplification procedure can be used, for example, in polymerase chain reaction (PCR) assays, strand displacement amplification and other amplification procedures. Strand displacement amplification can be used as described in Walker et al (1992) Nucl. Acids Res. 20, 1691–1696. The term "polymerase chain reaction" ("PCR") refers to the method of K. B. Mullis U.S. Pat. Nos. 4,683,195; 4,683,202; and 4,965,188, hereby incorporated by reference. These references by Mullis describe a method for increasing the concentration of a segment of a target sequence in a mixture of genomic or other DNA without cloning or purification.

The PCR process for amplifying a target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To do amplification, the mixture is denatured and the primers are annealed to complementary sequences within the target molecule. Following annealing, the primers are extended with a polymerase so as to form a new pair of complementary strands. The steps of denaturation, primer annealing and polymerase extension are termed a "cycle." There can be numerous cycles, and the amount of amplified DNA produced increases with each cycle. Hence, to obtain a high concentration of an amplified target nucleic acid, many cycles are performed.

The steps involve in PCR nucleic acid amplification method are described in more detail below. For ease of discussion, the nucleic acid to be amplified is described as being double-stranded. However, the process is equally useful for amplifying a single-stranded nucleic acid, such as an mRNA, although the ultimate product is generally double-stranded DNA. In the amplification of a single-stranded nucleic acid, the first step involves the synthesis of a complementary strand using, for example, one of the two amplification primers. The succeeding steps generally proceed as follows:

(a) Each nucleic acid strand is contacted with four different deoxynucleoside triphosphates and one oligonucleotide primer for each nucleic acid strand to be amplified, wherein each primer is selected to be substantially complementary to a portion the nucleic acid strand to be amplified, such that the extension product synthesized from one primer, when it is separated from its complement, can serve as a template for synthesis of the extension product of the other primer. To promote the proper annealing of primer(s) and the nucleic acid strands to be amplified, a temperature that allows hybridization of each primer to a complementary nucleic acid strand is used.

(b) After primer annealing, a DNA polymerase is used for primer extension that incorporates the nucleoside triphosphates into a growing nucleic acid strand that is complementary to the strand hybridized by the primer. In general, this primer extension reaction is performed at a temperature and for a time effective to promote the activity of the enzyme and to synthesize a "full length" complementary nucleic acid strand, that extends into a through a complete second primer binding. However, the temperature is not so high as to separate each extension product from its nucleic acid template strand.

(c) The mixture from step (b) is then heated for a time and at a temperature sufficient to separate the primer extension products from their complementary templates. The temperature chosen is not so high as to irreversibly denature the DNA polymerase present in the mixture.

(d) The mixture from (c) is cooled for a time and at a temperature effective to promote hybridization of a primer to each of the single-stranded molecules produced in step (b).

(e) The mixture from step (d) is maintained at a temperature and for a time sufficient to promote primer extension by DNA polymerase to produce a "full length" extension product. The temperature used is not so high as to separate each extension product from the complementary strand template. Steps (c)–(e) are repeated until the desired level of amplification is obtained.

The invention also comprises reagents and kits for detecting the presence of dGTPase nucleic acids or polypeptides in a sample. One reagent or kit can comprise purified antibodies of the invention in a liquid that does not adversely affect the activity of the antibodies in the intended assay, for example, a saline solution. Another reagent or kit can comprise isolated nucleic acids of the invention in a liquid that does not adversely affect the hybridization of the nucleic acids in the intended assay. Yet another reagent or kit can comprise isolated polypeptides of the invention in a liquid that does not adversely affect the activity of those polypeptides in the intended assay. Alternatively, the reagent or kit may comprise the purified antibodies, polypeptides or nucleic acids attached to a substrate as discussed above. Desired substrates are insoluble solid supports, e.g., the biosensors described herein or the well(s) of a microtiter plate.

Thus, in one embodiment the present invention provides a kit that includes a biosensor or solid support of the invention with an attached antibody that is capable of binding to a dGTPase of an Enterobacteriaceae. The kit can contain control samples. Control samples include, for example, one or more samples of Enterobacteriaceae dGT-Pases. The kit can also contain solutions for conducting the methods of the invention, for example, solutions for diluting test samples, for incubating test samples with the biosensor or antibody-solid support, and for washing off any unbound test sample. The kit may also comprise a blocking agent that is contacted with the biosensor prior to or during contact with the sample. Desired control and other solutions are sterile and free of substances that may interfere with detection of bound dGTPase.

In another embodiment, the present invention provides a kit that includes a biosensor or solid support of the invention with an attached nucleic acid probe that is capable of binding to a dGTPase nucleic acid in a test sample which may contain one or more species of Enterobacteriaceae. The kit can contain control samples. Control samples include, for example, one or more samples of Enterobacteriaceae dGT-Pase nucleic acids. The kit can also contain solutions for conducting the methods of the invention, for example, solutions for diluting test samples, for incubating test samples with the biosensor or solid support, and for washing off any unbound test sample. Desired control and other solutions are sterile and free of substances that may interfere with detection of dGTPase nucleic acids.

A label or reporter molecule that permits the antigen-antibody or the hybridization complex can also be provided with any of the kits of the invention. Such a label or reporter molecule can be packaged separately from the biosensor, nucleic acid or antibody.

An illustrative diagnostic system in kit form embodying one aspect the present invention that is useful for detecting dGTPase nucleic acids, is at least one container or vial containing a nucleic acid probe of the invention, for example, a nucleic acid having one of more of SEQ ID NO:2–18.

Labeled Nucleic Acids, Polypeptides and Antibodies

The invention utilizes labeled antibodies, labeled nucleic acid probes, and labeled dGTPase polypeptides. Labels that may be employed include radionuclides, fluorescent labels, chemiluminescent labels, colorimetric dyes, enzymes, enzyme substrates, enzyme cofactors, enzyme inhibitors, enzyme subunits, metal ions, particles, and the like. Radioisotopes commonly used as reporter molecules or labels include $^{32}P$, $^{125}I$ and $^{131}I$. Enzymes commonly used as reporter molecules or labels include such as alkaline phosphatase, horseradish peroxidase, beta-D-galactosidase and glucose oxidase. Commonly used fluorescent reporter molecules or labels include, for example, dyes such as fluorescein isothiocyanate (FITC), fluorescein, rhodamine, rhodamine B isothiocyanate (RITC), tetramethylrhodamine isothiocyanate (TRITC), 4,4'-diisothiocyanostilbene-2,2'-disulfonic acid (DIDS). See, for example, U.S. Pat. Nos. 3,766,162; 3,791,932; 3,817,837; and 4,233,402. Other commonly used types of labels or reporter molecules include Texas red, phycoerythrin, umbelliferone, luminol, NADPH, and the like.

Various techniques can be employed for detecting and quantifying the presence of the label which are dependent upon the nature of the label. For fluorescent labels, a large number of different fluorometers and flourescent microscopes are available. For chemiluminescent labels, luminometers or films are available. Enzymes producing a fluorescent, chemiluminescent, or colored product can be detected fluorometrically, luminometrically, spectrophotometrically or visually. Such labels can be employed in immunoassays and hybridization assays described herein.

Various means for providing labels bound to nucleic acids have been reported, e.g., Leary et al., Proc. Natl. Acad. Sci.

(USA) (1983) 80:4045; Renz and Kurz, Nucl. Acid Res. (1984) 12:3435; Richardson and Gumport, Nucl. Acid Res. (1983) 11:6167; Smith et al., Nucl. Acid Res. (1985) 13:2399; and Meinkoth and Wahl, Anal, Biochem. (1984) 138:267. The labels may be bound either covalently or non-covalently to the complementary sequence. Thus, for example, various labels may be attached to an antibody, nucleic acid or polypeptide via a carboxy, thiol, amine, hydrazine or other functionality without detrimentally affecting complex formation or hybridization of those entities.

The invention will be further described by the following examples.

EXAMPLE 1

Materials and Methods

General Procedures

All bacterial strains were purchased from the American Type Culture Collection (ATCC). The ATCC deposit numbers of the strains are listed in Table 5. Bacterial growth conditions and culturing were performed as described by Miller (18). Protein concentration was determined according to the method of Bradford (19) using bovine serum albumin (BSA) as a standard or spectrophotometrically using a calculated molar absorption coefficient of 86,300 $M^{-1}$ $cm^{-1}$ (20). All protein concentrations were for the dGTPase tetramer.

Analytical gel filtration experiments were performed according to Siegel and Monty (21) using Sephacryl S-300. Protein SDS PAGE gels were made, run, and processed as per Laemmli (22).

Single-stranded DNA binding assays were performed according to Wurgler and Richardson (23). Polymerase chain reaction (PCR) amplification of DNA was performed using VENT thermopolymerase from New England Biolabs, Inc. according to the instructions provided by the manufacturer. All PCR reactions were carried out in a ProGene thermocycler from Techne, Inc.

Enzyme Assay Procedures

Enzyme assay procedures were performed in a manner similar to those described by Seto et al. (13) by measuring the hydrolysis of dGTP to Norit non-adsorbable PPPi. The incubation mixture had a volume of 55 μL and included 2.0 mM dGTP; 67 mM Glycine, pH 8.5; 6.7 mM MgCl2; and 0.02–0.2 milliunit of enzyme. After 20 min at 37° C., the reaction was terminated by addition of an acidic suspension of Norit A. The mixture was centrifuged, and an aliquot of the supernatant was brought to 0.15 N HCl, and was boiled for 15 minutes. This step in the procedure resulted in the hydrolysis of tripolyphosphate to orthophosphate. The total orthophosphate concentration was determined calorimetrically by the addition of an ascorbate-molybdate solution. The absorbance at 780 nm was determined after incubating the mixture at 45° C. for 15 minutes. Results were compared to a phosphate standard curve. A unit of enzyme forms 1 μmol of tripolyphosphate under these conditions. The stimulatory effect of ssDNA was assayed by adding 50 μg/mL of m13 mp18 DNA to the standard assay.

Purification of Native E. coli dGTPase

Cells were grown at 37° C. in Luria broth from a 1% innoculum for ten hours before harvesting. Typically, 4 g of cells were obtained per liter. Cells were pelleted by centrifugation at 10,000×g for ten minutes and resuspended in one volume of 10 mM Tris-HCl, pH 8.0. The cells were respun as above and resuspended in two volumes of 10 mM Tris, pH 8.0, 1 mM EDTA, 1 mM sodium azide (Buffer I). The cells were disrupted by sonication on ice using a Branson sonicator. The extract was clarified by centrifugation at 12,000×g for 20 minutes, and the supernatant was designated as Fraction I. All subsequent chromatography steps were performed at room temperature.

Fraction I was heated in a water bath at 60° C. for 20 minutes with gentle swirling. During this period a large precipitate formed. After this heat treatment, the protein solution was immediately cooled to 4° C. in an ice bath. The supernatant was clarified by two successive centrifugations at 15,000×g for 30 minutes each. The protein in the decanted supernatant fraction from the second centrifugation step was designated as Fraction II.

Fraction II was applied to a 4.9 $cm^2$×30 cm column of DEAE Sepharose (Sigma Chemical Co.) in Buffer I. The enzyme was eluted from the column with a concave gradient of 0 to 0.5 M KCl at a flow rate of 2.0 ml/min. The major peak containing dGTPase activity eluted as a broad peak centered at 0.35 M KCl. The central 90% of the activity peak was pooled and constituted Fraction III.

This material was immediately applied to a single-stranded DNA cellulose column (4.9 $cm^2$×15 cm) that was equilibrated in Buffer I. After loading, the column was washed with five column volumes of Buffer I followed by 10 column volumes of Buffer I, 1.0 M KCl. Active dGTPase was eluted from the column with 10 column volumes of Buffer I, 3.0 M KCl. The homogeneous enzyme was concentrated via pressure filtration through a semipermeable membrane (Amicon YM 3) and dialyzed into new buffer constituents as needed.

Purification of native S. marcescens dGTPase

Enzyme from Serratia cultures was prepared to Fraction III as described above. Because this enzyme cannot bind to ssDNA, an alternative purification strategy was employed. Fraction III was loaded onto a prepacked Mono Q column (BioRad Labs Inc., column volume 1.0 mL), which was equilibrated with Buffer I. Elution was with a 50 mL linear zero to 1.0 M NaCl gradient at a flow rate of 3.0 mL/min. Functional dGTPase eluted from the column about halfway through the gradient. The first 90% of the activity peak was pooled, dialyzed versus Buffer I at 4° C., and constituted Fraction IV.

Fraction IV was applied to a prepacked Mono S column (BioRad, Inc.; column volume 1.0 mL) that had been equilibrated with Buffer I. The enzyme was eluted from the column with a 50 mL concave gradient from zero to 2.0 M KCl at a flow rate of 2.0 mL/min. The enzyme eluted from the column during the first quarter of the gradient. The central 95% of the activity peak was pooled and constituted Fraction V.

The final purification step consisted of applying Fraction V dGTPase (without prior dialysis) to a 90 cm×4.9 $cm^2$ Sephacryl 200-HR size exclusion column in Buffer I. The entire eluting dGTPase peak (as visualized by SDS-PAGE) was pooled and constituted homogeneous, Fraction VI enzyme. The enzyme was concentrated via pressure filtration through a semipermeable membrane (Amicon YM 3) and dialyzed into new buffer constituents as needed. All subsequent investigations were performed with Fraction VI protein.

Recombinant Enzyme Expression

Expression was performed with the T7 RNA polymerase over-expression system from Novagen, Inc., using the pET11d vector. A 1% innoculum of BL21(DE3)-pLysS cells containing expression plasmid constructs (pEdgte for *E. coli*, and pSdgte for *S. marcescens*) was grown at 37° C. in Luria broth supplemented with 60 mg/mL ampicillin. IPTG was added to a final concentration of 0.5 mM when the cells had reached an A595 value of 0.8 (in approximately three hours post inoculation). Cell growth continued for five additional hours before harvesting. Enzymes were purified as described above.

Production of Polyclonal Antibodies

Anti-dGTPase polyclonal antibodies (pAb) were produced against either *Escherichia* or *Serratia* dGTPase. Neutralizing anti dGTPase antibodies were induced by subcutaneous injection of homogeneous dGTPase (300 mg) in a 1:1 homogenate with Freund"s complete adjuvant into female New Zealand White rabbits. Three subsequent injections of antigen (200 mg) with incomplete adjuvant were performed at weekly intervals. One week after the last injection, the rabbits were bled via an ear cannula. The cleared plasma was collected by centrifugation at 14,000×g and stored at 4° C. until use.

Purification of Polyclonal Antibodies

The pAbs were purified to homogeneity by affinity chromatography on DEAE Affi-gel Blue. A BioRad Labs, Inc. rabbit polyclonal antibody isolation kit was employed according to the supplied instructions, with several minor modifications. The protocol was as follows: The cleared rabbit serum (5 mLs) was passed over an Econo-Pac 10DG desalting column. The pAbs were eluted from the column using the supplied running buffer (0.02 M Tris HCl (pH 8.0), 0.028 M NaCl), and were collected as a single fraction. The protein concentration was determined using the Bradford assay.

The entire serum sample (about 25 mLs) was passed over the column in 5 mL batches. Between batches, the column was washed with 40 mL of running buffer (two column volumes). The final desalted samples from the individual column runs were pooled. This pooled sample was applied to the DEAE Affi-gel Blue as a single load, the column was washed with 5 column volumes of running buffer (50 mLs), and the pAb fraction was eluted from the column by the application of 5 column volumes of elution buffer (0.025 M Tris HCl (pH 8.0), 0.025 M NaCl). The eluted material was collected as 5 mL fractions. Purity of the IgG fraction was estimated by SDS PAGE. Appropriate fractions were pooled, concentrated to 2 mg/mL by pressure filtration, and stored at −70° C. until needed. The DEAE Affi-gel Blue column was regenerated by washing the column with 2 M NaCl, 1.5 M sodium thiocyanate in running buffer (10 column volumes), followed by re-equilibration in running buffer. The flow rate for all chromatography steps was maintained at 1.0 mL/min.

ELISAs and Western Blot Analysis

ELISAs were performed according to Kaiser and Pollard, (24) or according to Quirk et al. (25). Ten μg of partially purified protein extract, or 1 μg of purified dGTPase was adsorbed to the surface of a 96-well microtiter plate (Immulon 2, Dynatech Labs). After the wells were blocked with phosphate buffered saline (PBS) supplemented with 10% nonfat dry milk, polyclonal antibodies in blocking buffer were added at various dilutions and were allowed to react with the antigen at room temperature for one hour. Following three washes in PBS, visualization was achieved via a goat anti-rabbit secondary antibody that was conjugated with horse radish peroxidase (Santa Cruz Biotechnology, Inc.). The secondary antibody was added at a 1:2000 dilution in blocking buffer and was incubated at room temperature for one hour. After three washes in PBS, color development was achieved by adding a solution containing 50 mM sodium citrate, 50 mM citric acid, 1 mg/mL o-phenylenediamine, and 0.006% H2O2. After suitable color development (typically 5 to 10 minutes of incubation at room temperature) 50 μL of 2 M sulfuric acid was added to stop the reaction and stabilize the product. Absorbance was measured at 490 nm using an automatic ELISA plate reader (Molecular Dynamics, Inc.). Western blots were made according to (26) and were used to assay antibody specificity and cross reactivity.

Conjugation of the pAb Pool to CNBr Activated Agarose

CNBr activated agarose resin (Sigma Chemical Co.) was preswollen in approximately 200 mLs of 0.001 N HCl at room temperature immediately prior to use. The coupling capacity of the resin was 1 g dry resin for every 10 mg of protein. The purified pAb pool was dialyzed against coupling buffer (0.1 M $H_3BO_3$, 25 mM $Na_2B_4O_7$, 75 mM NaCl, pH 8.4) overnight at 4° C. The resin was poured into a scintered glass funnel and was washed extensively with coupling buffer (approximately 25 mLs of buffer per 1 mL of resin). The resin was removed from the filter and was mixed with the pAb pool. This mixture was incubated with constant gentle rocking at room temperature for 4 hours, followed by an overnight incubation at 4° C. The resin was collected on the glass filter. The protein concentration in the saved filtrate was determined via Bradford assay in order to calculate the coupling yield (usually greater than 90%). The immunoaffinity resin was removed from the filter and was resuspended in 15 mL of 1 M ethanolamine (pH 8.0) in order to block remaining unreacted CNBr groups. After incubation for two hours at room temperature (with gentle constant shaking), the resin was collected on the glass filter and was extensively washed (usually 10 volumes each) with borate buffer (0.1 M $H_3BO_3$, 25 mM $Na_2B_4O_7$, 1 M NaCl; pH 8.4), followed by acetate buffer (75 mM $NaCOOCH_3$, 1 M NaCl). Non covalently bound protein was removed with this washing step. Finally, the resin was washed (usually 10 volumes) with coupling buffer, and was resuspended in an excess volume of Tris buffered saline (TBS), pH 7.6 and was stored at 4° C. until use. The immunoaffinity resin was utilized to purify dGTPase from other genera of the Enterobacteriaceae as described below.

Isolation of Enteric dGTPases by Immunoaffinity Chromatography

Twenty mLs of immunoaffinity resin was utilized to purify enteric dGTPase from a 2 liter overnight culture (grown in LB media at 30° C. for 12 hours). A crude protein extract was prepared from this material as follows. Culture medium was centrifuged at 6,000×g in order to pellet the bacterial cells. The pellet was resuspended in 40 mLs of 30 mM glycine (pH 7.5) and recentrifuged. The final pellet was resuspended in 10 mLs of 30 mM glycine (pH 7.5) and was subjected to three cycles of sonication using a Branson sonicator equipped with a microtip. All procedures were carried out at 4° C. unless otherwise specified. The sonicated material was centrifuged at 10,000×g for 20 minutes, and the supernatant was decanted and retained.

This crude protein extract was heated to 60° C. for 15 minutes with gentle swirling. During this incubation period a milky white precipitate formed. The material was clarified by centrifugation at 10,000×g for 20 minutes. The supernatant was again decanted and retained. The crude extract was mixed with 0.1 volume of 5% streptomycin sulfate, was incubated on ice for 60 minutes, and was centrifuged at 12,000×g for 20 minutes. The pellet was triturated with 2 mLs of 30 mM Kpi (pH 7.5) with gentle mixing and agitation, and then was recentrifuged as before. The final supernatant was dialyzed overnight at 4° C. against 30 mM Kpi (pH 7.5). This material was then heated to 60° C. with gentle swirling for 15 minutes, was centrifuged at 10,000×g for 20 minutes, and the supernatant was decanted. The protein fraction was then combined with the affinity resin preparation, and incubated on ice for eight hours with occasional swirling. The slurry was poured into a column. The column was washed with 50 mLs of 20 mM glycine (pH 7.5), followed by 20 mLs of 20 mM glycine (pH 7.5), 3 M potassium thiocyanate at a flow rate of 10 mLs per hour. Eluted protein was collected as a single fraction and immediately concentrated to a volume of 0.1 mL by pressure filtration through a semi permeable membrane (Amicon). The final sample was then extensively dialyzed versus 20 mM KPi (pH 7.5) at 4° C. Several such rounds of purification were performed in order to have sufficient material for studies.

Biosensor Chip Design

A CM5 unmodified biosensor chip (27) was obtained from BiaCore, Inc. This chip was a 1 cm square quartz crystal that was coated with a thin gold layer. Attached to the gold layer was a tether of carboxymethyldextran. The terminal carboxyl groups are easily modified in order to create reactive groups for protein coupling. The linkage reaction began with the activation of the chip tether. The chip was reacted with a solution of 100 mM N-ethyl-N'(dimethylaminopropyl) carbodiimide hydrochloride (EDC) and 50 mM N-hydroxysuccinimide (NHS) in 25 mM sodium bicarbonate (pH 8.5) for 5 minutes, followed by a brief rinse with 100 mM borate (pH 8.5). The activated CM5 chip was incubated in 80 mM 2-(2-pyridinyldithio)ethaneamine (PDEA), 0.1 M borate (pH 8.5) for four minutes, followed by a brief rinse in 0.1 M borate (pH 8.5). The chip was then placed in contact with a solution (200 μl) containing purified pAb at a concentration of 0.05 mg/mL for 10 minutes. Finally, all reactive disulfides were deactivated, and non-covalently bound protein was removed by soaking the chip surface in 200 μL of 50 mM cysteine, 1 M NaCl for 10 minutes. All reactions were done at room temperature. The final biosensor was used in a BiaCore surface plasmon instrument according to the instructions from the manufacturer. Flow rate over the sensor surface was 50 μL per minute.

EXAMPLE 2

Immunological Relationship between Enterobacteriaceae dGTPases

The immunological relatedness of dGTPase among several Enterobacteriaceae genera was examined by using purified anti-dGTPase polyclonal antibodies (pAbs) combined with an enzymatic assay for the protein. This approach was highly sensitive and specific for dGTPase activity. Table 5 provides the specific activities and generalized antibody reactivities of dGTPases from several genera of Enterobacteriaceae that were partially purified as described in Example 1 (Fractions II and III). Immunological reactivities with two separate antibody preparations were observed: anti-*Escherichia coli* dGTPase and anti-*Serratia marcescens* dGTPase.

TABLE 5

| Bacterial Type | | Specific Activity (units/mg) | | pAB Reactivity[1] | |
| --- | --- | --- | --- | --- | --- |
| Bacterial Species | ATCC No. | Fraction II | Fraction III | Anti-E | Anti-S |
| *Cedecea davisae* | 33431 | 1.4 | 20.0 | ++ | − |
| *Citrobacter freundii* | 8090 | 0.8 | 15.0 | + | − |
| *Enterobacter aerogens* | 13048 | 0.6 | 11.0 | − | +++ |
| *Escherichia coli* | 25257 | 1.3 | 27.0 | +++ | − |
| *Escherichia coli* O157:H7 | 35150 | 1.2 | 25.0 | +++ | − |
| *Escherichia coli* O111 | 33780 | 1.3 | 26.0 | +++ | − |
| *Escherichia coli* O124:NM | 43893 | 1.3 | 25.8 | +++ | − |
| *Escherichia fergusonii* | 35469 | 1.2 | 26.2 | +++ | − |
| *Hafnia alvei* | 29926 | 0.5 | 9.0 | − | ++ |
| *Klebsiella oxytoca* | 43165 | 2.3 | 20.6 | + | − |
| *Klebsiella pneumoniae* | 13883 | 2.2 | 20.2 | + | − |
| *Proteus mirabilis* | 7002 | 3.1 | 19.9 | − | + |
| *Proteus vulgaris* | 13315 | 2.8 | 18.6 | − | ++ |
| *Salmonella enteritidis* | 13076 | 1.5 | 14.8 | ++ | − |
| *Salmonella gallinarum* | 9184 | 1.7 | 14.2 | ++ | − |
| *Salmonella typhi* | 6539 | 1.2 | 14.3 | ++ | − |
| *Salmonella typhimurium* | 14028 | 1.1 | 14.0 | ++ | − |
| *Serratia marcescens* | 8100 | 1.6 | 17.3 | − | +++ |
| *Serratia odorifera* | 33077 | 1.5 | 17.0 | − | +++ |
| *Shigella boydii* | 9207 | 2.4 | 19.7 | +++ | − |
| *Shigella dysenteriae* | 13313 | 2.3 | 19.0 | +++ | − |
| *Yersinia enterocolitica* | 23715 | 0.6 | 8.4 | − | +++ |
| *Yersinia intermedia* | 29909 | 0.8 | 9.1 | − | +++ |

[1]Relative reactivity is measured by the loss of enzymatic activity as a function of either anti *E. coli* (E) or anti *S. marcescens* (S) dGTPase polyclonal antibodies. +++ is highly reactive; ++ is moderately reactive; + is slightly reactive; − is not reactive.

Enzyme specific activities ranging from slightly lower to slightly higher than that observed for the dGTPase from *E. coli* were seen. All of the enteric dGTPases exhibit similar fractionation behavior throughout the partial purification protocol, suggesting that many of the physico-chemical properties of the various dGTPases were similar. However, as indicated in Table 5, the immunological reactivities of the various dGTPases were not identical.

Moreover, an antibody raised against one type of dGTPase could inhibit enzyme activity of dGTPases from only a subset of Enterobacteriaceae genera. Polyclonal antibodies produced against either the *E. coli* or the *S. marcescens* enzyme tested for their ability to inhibit dGTPase activity among various bacteria. As illustrated in FIGS. 1–4, the ability of an antibody to inhibit dGTPase activity was dependent on the source of antigen used to generate the antibody. The dependence of antibody inhibition upon the concentration of pAb is also illustrated in FIGS. 1–4.

Figure 1:
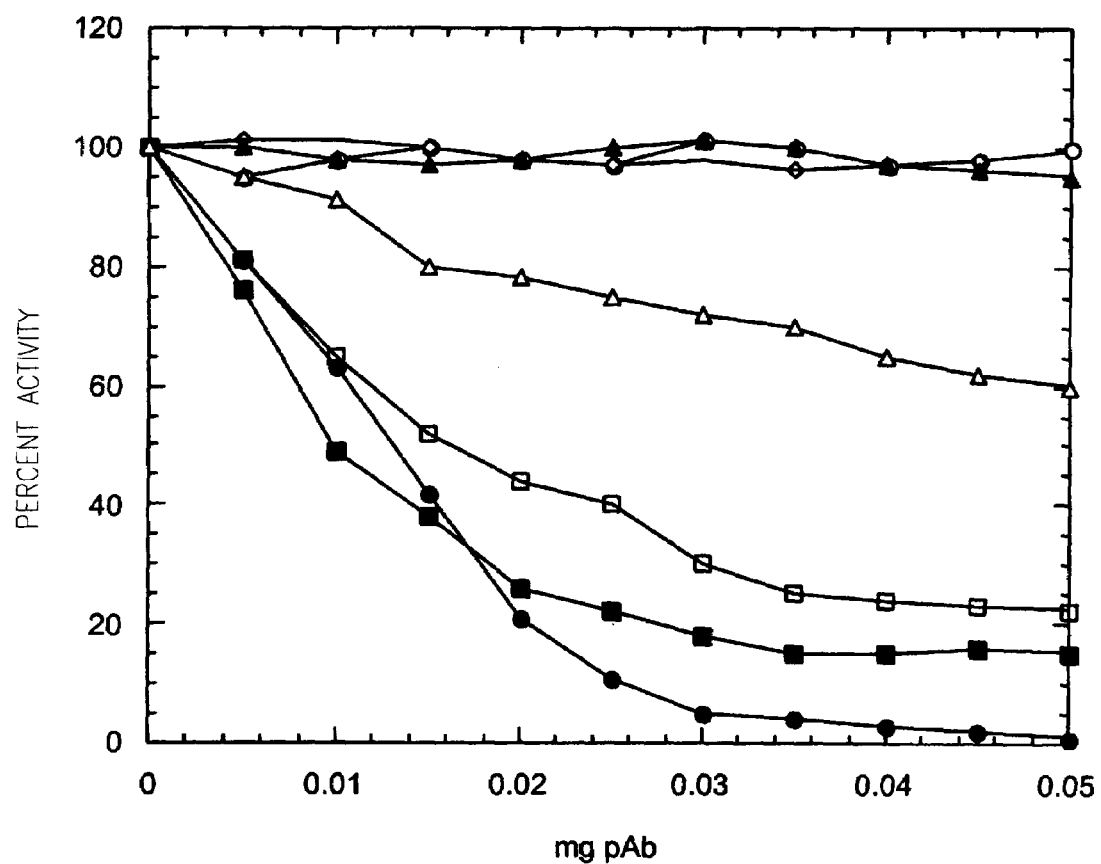
FIG. 1 illustrates the loss of activity in enzyme preparations from several species of Enterobacteriaceae as a function of increasing amounts of anti-dGTPase polyclonal antibody (pAb). The anti-dGTPase polyclonal antibody was raised against dGTPase isolated from *E. coli*. Inhibition of dGTPase isolated from *Y. enterocolitica* (open circles), *E. aerogens* (closed triangles), *P. vulgaris* (open diamonds) *K. oxytoca* (open triangles), *S. typhimurium* (open squares), *S. boydii* (closed circles), and *C. davisae* (closed squares) by the anti-dGTPase pAb is shown.

FIG. 1 shows the effect of anti-*E. coli* dGTPase polyclonal antibodies upon enzymatic activity of dGTPases isolated from *Y. enterocolitica* (open circles), *E. aerogens* (closed triangles), *P. vulgaris* (open diamonds) *K. oxytoca* (open triangles), *S. typhimurium* (open squares), *S. boydii* (closed circles), and *C. davisae*. Enzyme (Fraction III) was incubated with various amounts of pAb for 15 minutes at 25° C., followed by measurement of residual enzyme activity using a radioactive assay for the production of tripolyphosphate (16). Percent activity of a control enzyme preparation (no added pAb) was arbitrarily set to 100 percent. Three of the tested enteric genera, *Salmonella, Shigella*, and *Cedecca* were effectively inhibited by anti-*Escherichia* pAbs. Three of the tested genera, *Proteus, Yersinia* and *Enterobacter*, were not inhibited by the addition of the pAb preparation. *Klebsiella* was inhibited by the addition of anti-*Escherichia* pAbs, but only half as effectively as the *Salmonella, Shigella*, and *Cedecca* genera.

Figure 2:
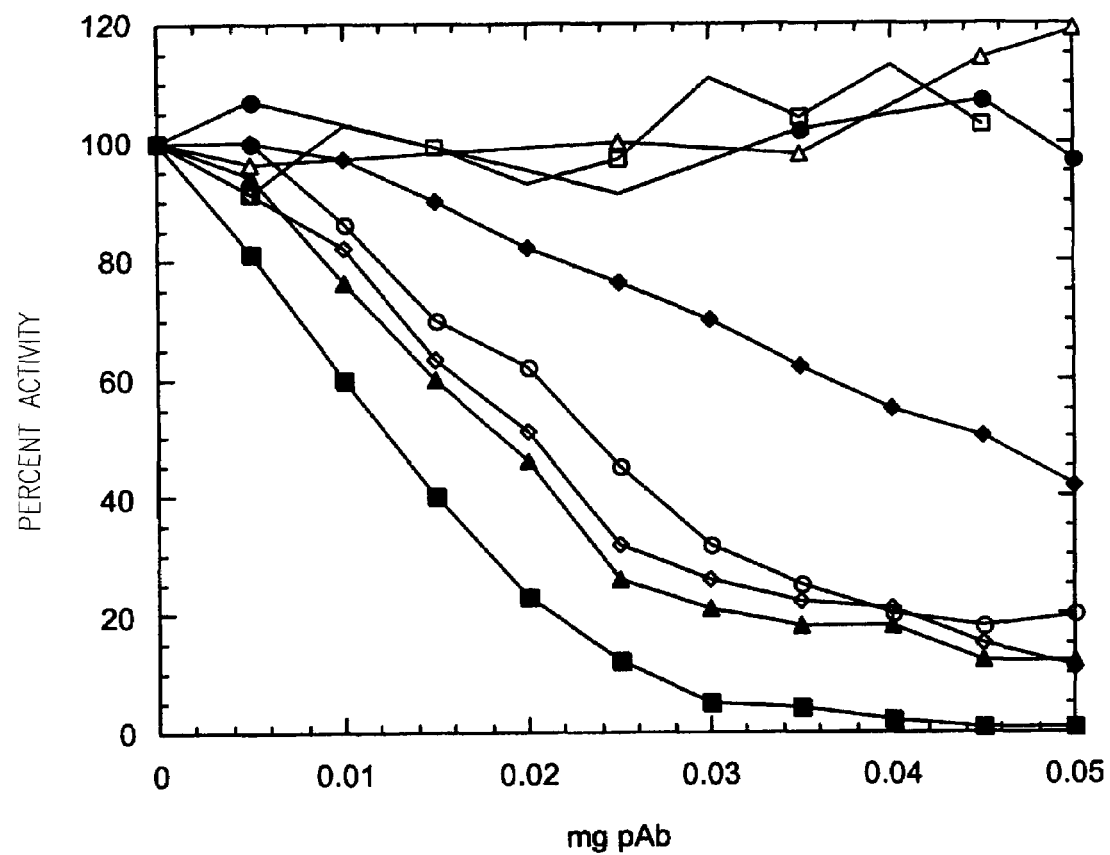
FIG. 2 illustrates the loss of activity in enzyme preparations from several species of Enterobacteriaceae as a function of increasing amounts of anti-dGTPase polyclonal antibody (pAb). The anti-dGTPase polyclonal antibody was raised against dGTPase isolated from *S. marcescens*. Inhibition of dGTPase isolated from *S. typhimurium* (open squares), *K. oxytoca* (open triangles), *S. boydii* (closed circles), *P. vulgaris* (open diamonds), *Y. enterocolitica* (open circles), *H. alvei* (closed diamonds), *E. aerogens* (closed triangles), and *S. marcescens* (closed squares) by the anti-dGTPase pAb is shown.

The ability of anti-*Serratia marcescens* dGTPase pAbs to inhibit the enzymatic activity of these dGTPases was assayed as above and is presented in FIG. 2. The enzyme activities of dGTPases isolated from *S. typhimurium* (open squares), *K. oxytoca* (open triangles), *S. boydii* (closed circles), *P. vulgaris* (open diamonds), *Y. enterocolitica* (open circles), *H. alvei* (closed diamonds), *E. aerogens* (closed triangles), and *S. marcescens* (closed squares) in the presence of anti-*Serratia marcescens* dGTPase is shown in FIG. 2. Anti-*Serratia marcescens* dGTPase pAbs do not significantly alter the enzymatic activity of *Klebsiella, Salmonella*, or *Shigella* genera. These antibodies were, however, effective in inhibiting the enzymatic activity of *Enterobacter, Yersinia*, and to a lesser extent, *Proteus*. The loss of enzymatic activity in the presence of pAb therefore provides an assay for the functional relatedness or cross reactivity of dGTPases from different species. It is also a relatively rapid assay with a sensitivity comparable to that of an ELISA analysis.

Figure 3:
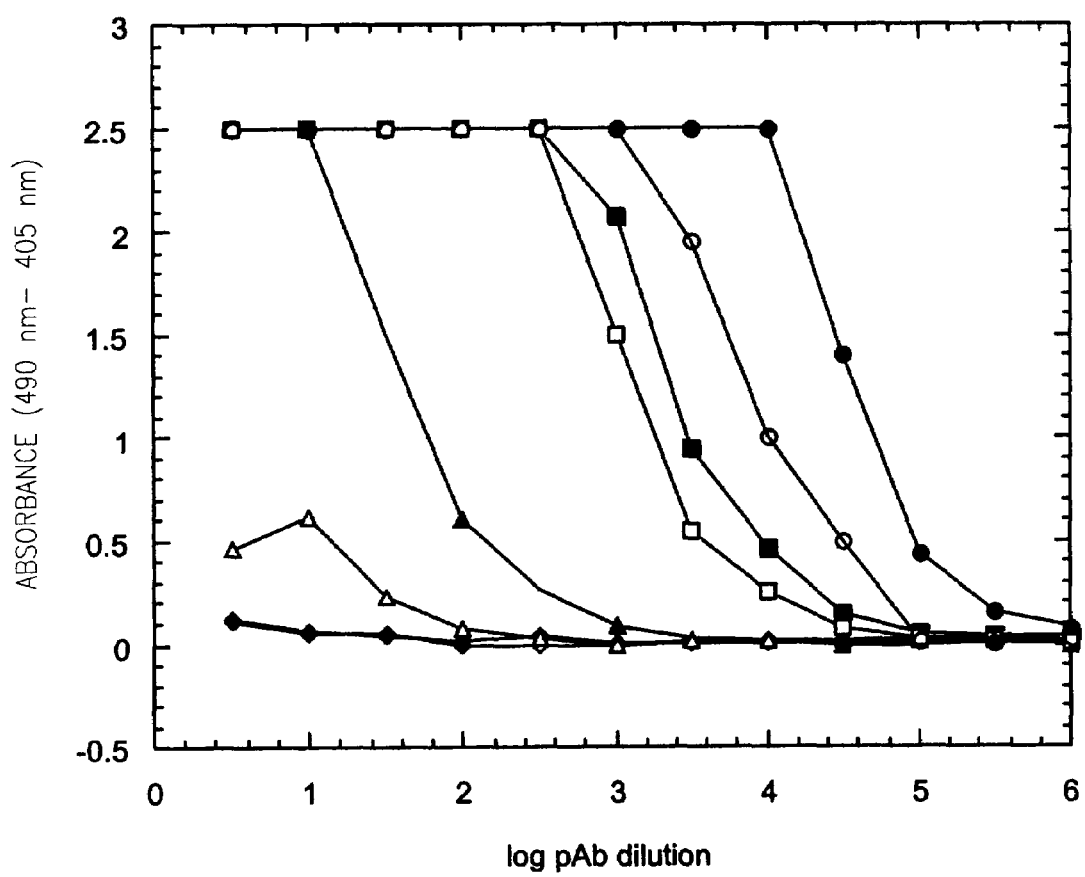
FIG. 3 provides results of an ELISA analysis of cross reactivity between anti-*E. coli* dGTPase pAb and 1 mg of an adsorbed Fraction III enzyme preparation from: *E. coli* O157 (closed circles), *S. boydii* (open circles), *S. typhimurium* (closed squares), *K. oxytoca* (closed triangles), *E. aerogens* (closed diamonds), *C. davisae* (open squares), *Y. enterocolitica* (open diamonds), and *C. freundii* (open triangles).

Further immunological cross reactivity was assayed by ELISA as shown in FIG. 3. The reactivity of anti-*Escherichia* dGTPase pAbs with immobilized dGTPases from *E. coli* 0157 (closed circles), *S. boydii* (open circles), *S. typhimurium* (closed squares), *K. oxytoca* (closed triangles), *E. aerogens* (closed diamonds), *C. davisae* (open squares), *Y. enterocolitica* (open diamonds), and *C. freundii* (open triangles) was observed by reacting a secondary antibody with any bound pAb. Anti-*Escherichia* dGTPase pAbs efficiently bind enzymes from *Shigella, Cedecca, Salmonella, Klebsiella*, and to a lesser extent, *Citrobacter*. The pAbs also bind to dGTPases from other *Escherichia* species. The ELISA assay shows no reactivity towards *Enterobacter* or *Yersinia* dGTPases.

Figure 4:
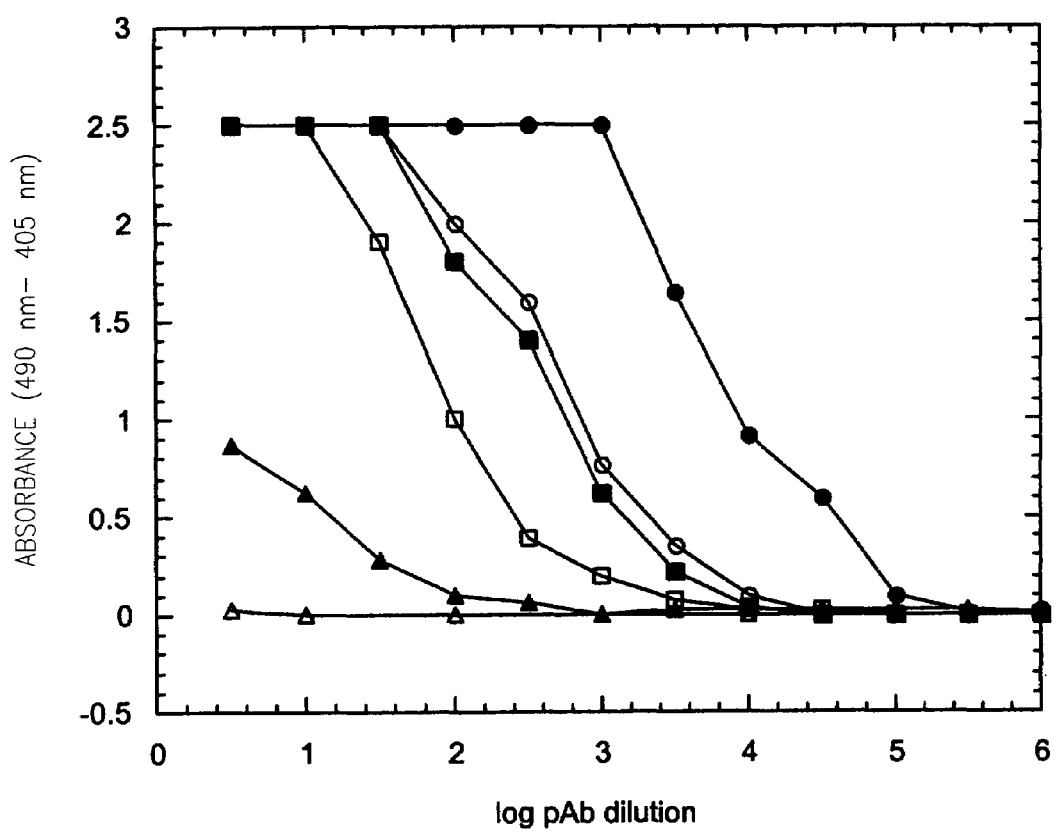
FIG. 4 provides results of an ELISA analysis of cross reactivity between anti *S. marcescens* dGTPase pAb and 1 mg of adsorbed Fraction III enzyme preparation from: *S. typhimurium* (closed triangles), *E. coli* (open triangles), *H. alvei* (open squares), *E. aerogens* (closed circles), *Y. enterocolitica* (open circles), and *P. vulgaris* (closed squares).

Anti-*Serratia* dGTPase pAbs binding to various dGTPases by ELISA assay is shown in FIG. 4. Fraction III enzyme preparation from *S. typhimurium* (closed triangles), *E. coli* (open triangles), *H. alvei* (open squares), *E. aerogens* (closed circles), *Y. enterocolitica* (open circles), and *P. vulgaris* (closed squares) was adsorbed onto microtiter plates and the amount of anti-*Serratia* dGTPase pAbs bound was detected with a secondary antibody. The anti-*Serratia* dGTPase antibody preparation efficiently detects antigen from *Enterobacter, Yersinia, Proteus*, and *Hafnia*. dGTPases from *Salmonella* and *Escherichia* were not detected with these anti-*Serratia* 2pAbs. These ELISA results were in complete accord with the loss of enzymatic activity shown in FIGS. 1 and 2, and summarized in Table 5.

Significantly, by using only antibody preparations from *Escherichia coli* and *Serratia marcescens*, it was possible to detect dGTPases from all major enteric genera. Moreover, by using just these two antibody preparations, it was possible to differentiate between the types of bacteria detected. Such differentiation can help identify which genus of bacteria is present in a test sample.

Figure 5A:
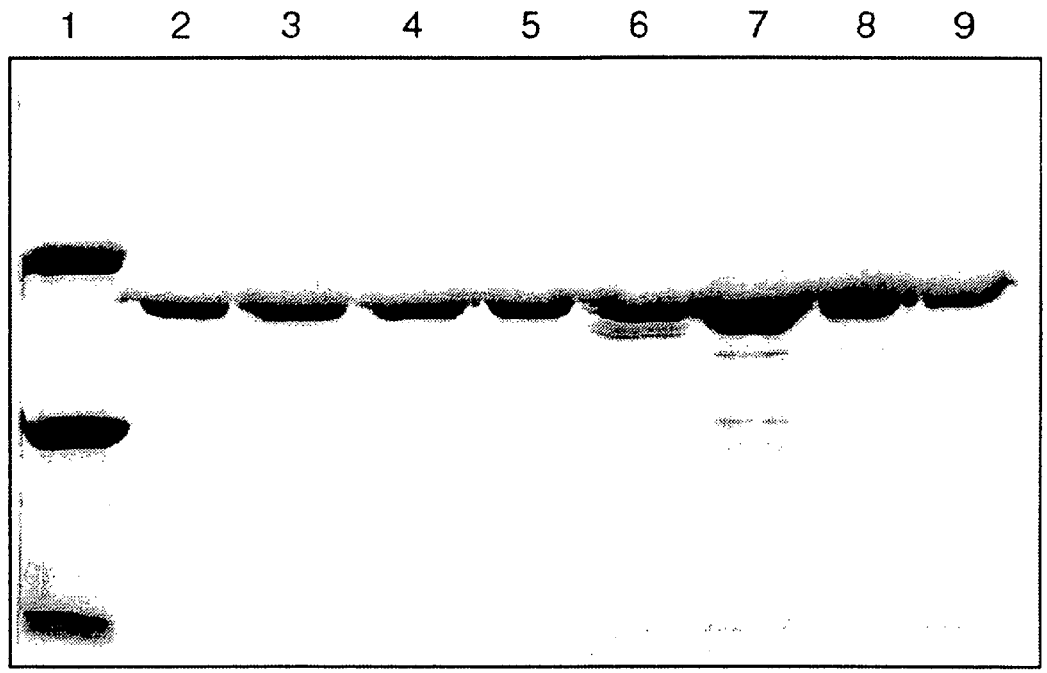
FIG. 5A provides an SDS PAGE analysis of enteric dGTPases from several species isolated using an immunoaffinity column chromatography column of anti-Escherichia dGTPase pAb (lanes 2–5) or anti-Serratia dGTPase pAb (lanes 6–9). Lane 1, molecular weight markers (65 kDa, 45 kDa, 24 kDa from top to bottom); Lane 2, *Salmonella*; Lane 3, *Shigella*; Lane 4, *Klebsiella*; Lane 5, *Cedecca*; Lane 6, *Yersinia*; Lane 7, *Proteus*; Lane 8, *Enterobacter*; Lane 9, *Hafnia*.

Anti-*Serratia* or anti-*Escherichia* immunoaffinity columns were employed to isolate nearly homogenous dGTPase preparations from nine enteric bacteria. FIG. 5A provides a SDS PAGE analysis of the immunoaffinity column-purified enzymes. Immunopurified dGTPases from nine species were all capable of hydrolyzing dGTP to deoxyguanosine and tripolyphosphate. They were all thermostable. All isolated dGTPases, with the exception of *Serratia* dGTPase, bind to single-stranded DNA. However, while most dGTPases are tetrameric, *Serratia* dGTPases are dimeric. These results are summarized in Table 6.

TABLE 6

| Bacterial Species | dGTPase | | Stability | Structure | ssDNA Binding | |
|---|---|---|---|---|---|---|
| | Km (µM) | kcat ($s^{-1}$) | t½ at 65° C. (min) | Quaternary structure | Ka ($M^{-1} \times 10^6$) | Stimulation (fold) |
| *C. davisae* | 7.9 | 3379 | 16.8 | tetramer | 5.3 | 1.5 |
| *E. aerogens* | 5.6 | 3720 | 23.0 | tetramer | 5.6 | 1.5 |
| *E. coli* O157.H7 | 6.2 | 4032 | 21.5 | tetramer | 6.3 | 1.7 |
| *E. coli* | 6.0 | 4020 | 22.0 | tetramer | 6.2 | 1.6 |
| *H. alvei* | 9.1 | 3655 | 17.5 | tetramer | 4.7 | 1.4 |
| *K. pneumoniae* | 6.0 | 4002 | 23.0 | tetramer | 6.0 | 1.5 |
| *P. vulgaris* | 3.7 | 4112 | 31.5 | tetramer | 7.1 | 1.9 |
| *S. enteritidis* | 6.2 | 3218 | 23.3 | tetramer | 6.1 | 1.6 |
| *S. marcescens* | 3.0 | 3975 | 18.7 | dimer | nd* | 1.0 |
| *Y. enterocolitica* | 5.8 | 3982 | 27.0 | tetramer | 7.0 | 1.8 |

* nd, no detectable binding

Figure 5B:
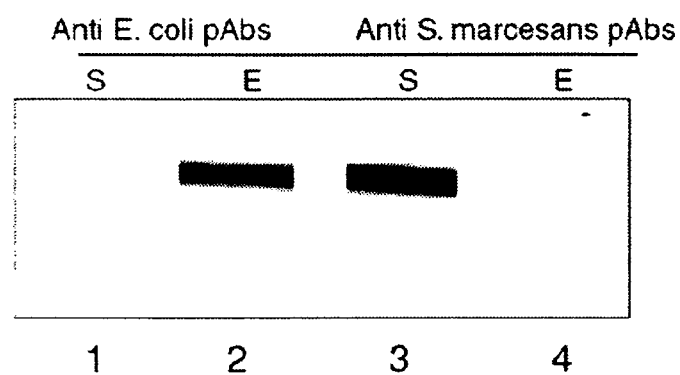
FIG. 5B provides a Western blot analysis using antibodies raised against two different isolates of dGTPase. Anti-*E. coli* dGTPase pAb was used for detection of dGTPase in crude *S. marcescens* protein extract (lane 1) and in crude *E. coli* protein extract (lane2). Anti-*S. marcescens* dGTPase pAb was used for detection of dGTPase in crude *S. marcescens* protein extract (lane 3) and in crude *E. coli* protein extract (lane 4).

FIG. 5B shows that the anti-*Serratia* and anti-*Escherichia* dGTPase antibodies used in these studies were specific for the detection of the dGTPase enzyme, and do not cross react with other bacterial proteins in crude extracts. Only a single band was observed on the Western blot shown in FIG. 5B, indicating that the anti-*Serratia* pAbs only detected *Serratia* dGTPase and the anti-*Escherichia* pAbs only detected *Escherichia* dGTPase. No cross-reactivity was observed. This observation is further supported by the enzymatic studies, where the anti-*Serratia* pAbs did not appreciably bind to the *Escherichia* dGTPase and did not inhibit enzymatic activity of dGTPases from genera related to *Escherichia*, and vice versa. Such immuno-specificity is highly desirable for construction of an accurate diagnostic test for enteric bacterial contamination.

EXAMPLE 3

Biosensor Chips for Detection of Enterobacteriaceae

Biosensor chips were made and utilized for easy detection of enteric dGTPases. Using the induced thiol coupling method described in Example 1, the surface of a CM5 chip was modified by attaching either anti-*Escherichia* or anti-*Serratia* dGTPase pAbs. These biosensors were employed for the detection of enteric dGTPases using a BiaCore 2000 surface plasmon resonance (SPR) device.

Figure 6:
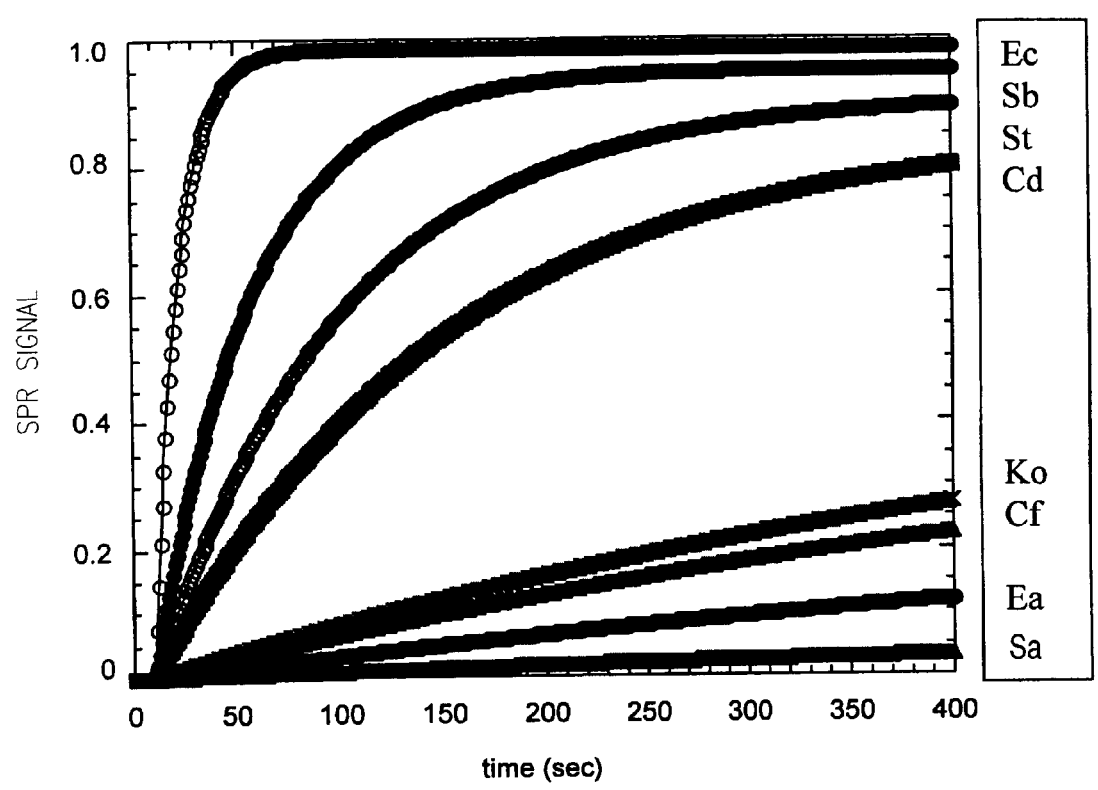
FIG. 6 provides an surface plasmon resonance (SPR) sensogram showing the reactivity of tethered pAbs against dGTPase from various bacteria. Relative SPR signal intensity is plotted as a function of time for anti-*E. coli* dGTPase pAbs reacted with crude bacterial extract of *E. coli* (Ec), *S. boydii* (Sb), *C. daviseae* (Cd), *K. oxytoca* (Ko), *S. typhimurium* (St), *C. freundii* (Cf), *E. aerogens* (Ea), and *S. aureus* (Sa) (non enteric bacterial control). Flow rate over the sensor surface was 50 μL per minute.
Figure 7:
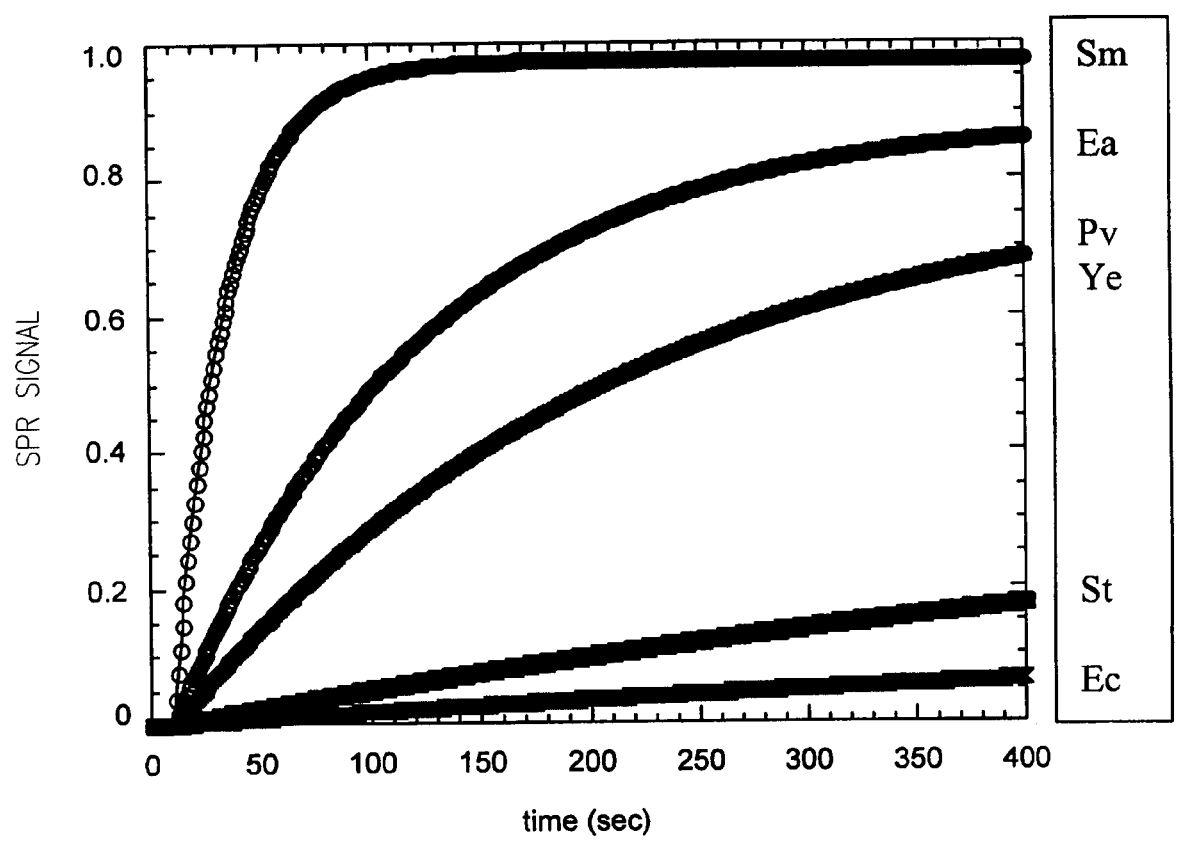
FIG. 7 provides an SPR sensogram showing the reactivity of tethered pAbs-against dGTPase from various bacteria. Relative SPR signal intensity is plotted as a function of time for: anti-*S. marcescens* dGTPase pAbs reacted with crude bacterial extract of *S. marcescens* (Sm), *E. aerogens* (Ea), *Y. enterocolitica* (Ye), *P. vulgaris* (Pv), *E. coli* (Ec), and *S. typhimurium* (St). Flow rate over the sensor surface was 50 μL per minute.

The results of these experiments are shown in FIGS. 6 and 7. FIG. 6 provides a surface plasmon resonance (SPR) sensogram showing the reactivity of tethered anti-*E. coli* dGTPase pAbs with crude bacterial extracts from *E. coli* (Ec), *S. boydii* (Sb), *C. daviseae* (Cd), *K. oxytoca* (Ko), *S. typhimurium* (St), *C. freundii* (Cf), and *E. aerogens* (Ea). As shown in FIG. 6, anti-*E. coli* dGTPase pAbs react most strongly with *E. coli* (Ec), *S. boydii* (Sb), *S. typhimurium* (St), and *C. daviseae* (Cd).

FIG. 7 provides a surface plasmon resonance (SPR) sensogram showing the reactivity of tethered anti-*Serratia marcescens* dGTPase pAbs with crude bacterial extracts from *S. marcescens* (Sm), *E. aerogens* (Ea), *Y. enterocolitica* (Ye), *P. vulgaris* (Pv), *E. coli* (Ec), and *S. typhimurium* (St). As shown in FIG. 7, anti-*Serratia marcescens* dGTPase pAbs react most strongly with *S. marcescens* (Sm), *E. aerogens* (Ea), *Y. enterocolitica* (Ye), and *P. vulgaris* (Pv).

The sensograms shown in FIGS. 6 and 7 are highly reproducible with standard deviations of +1% of signal intensity across the binding isotherm. The biosensor chips have been reused up to 10 times without degradation of the SPR signal.

Both biosensors chips have the ability to detect dGTPase in crude bacterial extract and they can discriminate between types of dGTPases. The binding interaction affinity observed in the SPR system mirrors that observed using the ELISA assay. In addition the biosensors can differentially detect bacterial genera as shown by the sensogram binding isotherms. There was nearly no detectable background binding (even using crude protein extract) as evidenced by the nearly flat binding isotherm for a gram positive, non enteric bacterium (*S. aureus*, marked Sa in FIG. 6.

Figure 8:
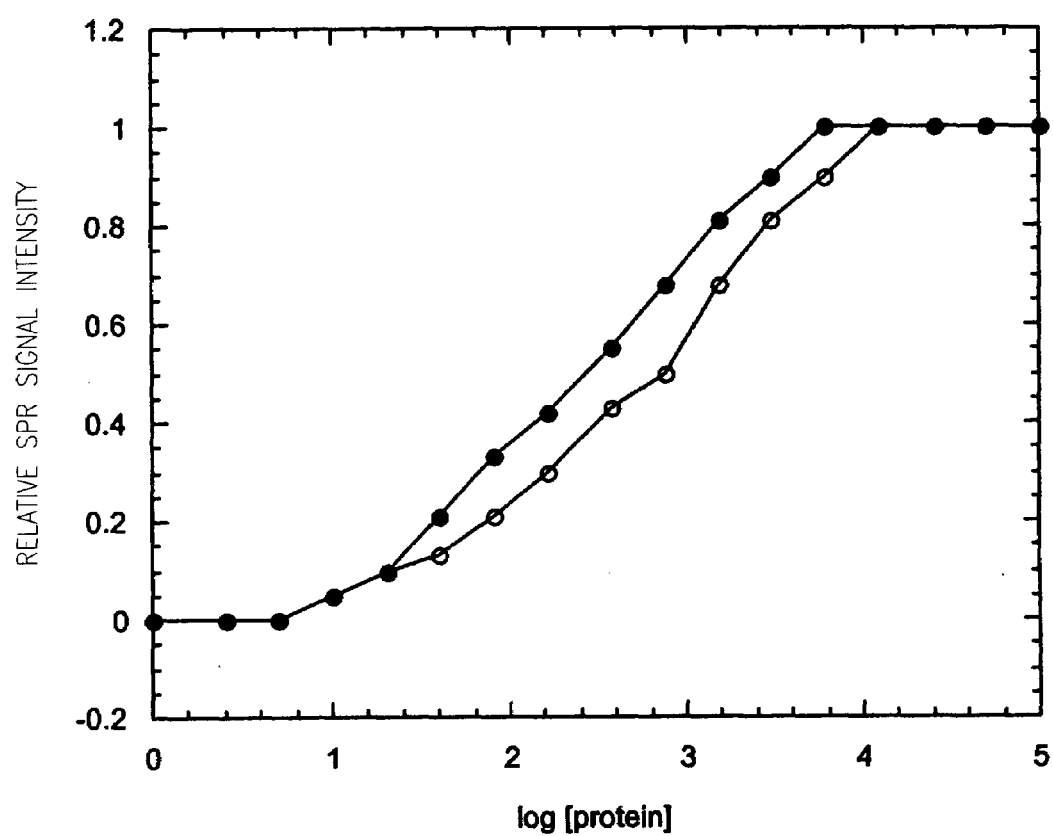
FIG. 8 provides a curve illustrating the titration of the SPR biosensors with purified dGTPase. The curves represent the relative SPR signal intensity for a given amount of enzyme reacted with the surface at 400 seconds (after binding is complete, see FIG. 6). In between sample points, the chip was washed with 2 M potassium thiocyanate in order to remove bound dGTPase, followed by a 10 minute buffer wash, followed by the next dGTPase concentration. The anti *E. coli* pAb surface (open circles) was reacted with *E. coli* dGTPase, and the anti *S. marcescens* pAb surface (closed circles) was reacted with *S. marcescens* dGTPase. The abscissa scale runs from 0 to 100 ng.

The chips used above were titrated with increasing amounts of dGTPase in order to determine the detection limit in the system. The results of this experiment are shown in FIG. 8. The chip with the anti-*Escherichia* pAbs was able to detect 1 μg of purified *E. coli* dGTPase. A similar detection limit was observed when the biosensor chip having anti-*Serratia* pAbs when it was reacted with purified *Serratia* dGTPase.

Hence, the polyclonal antibody preparations made as described herein were capable of specifically detecting low amounts of enzyme within the background of other bacterial proteins, all within 400 seconds. Such differential reactivities indicate not only that Enterobacteriaceae can be detected in complex test samples but that the type of Enterobacteriaceae can be identified.

EXAMPLE 4

PCR Detection and Identification of Enterobacteriaceae

The invention provides nucleic acids that can be used to detect Enterobacteriaceae and to identify which genus of Enterobacteriaceae is present in a sample. In this example, the nucleic acids are used in a series of polymerase chain reaction (PCR) amplification experiments to demonstrate the specificity and sensitivity of the present detection and identification methods.

Using the DNA sequence of the *E. coli* gene (SEQ ID NO:1, FIG. 9), PCR primers were identified and synthesized that could amplify any enteric dgt gene (Table 7). Separate PCR primers were identified and synthesized that could specifically amplify dgt sequences from a single enteric genus (Table 7a–7c). The primers were used in pairs that were labeled primer pairs 1 to 13, as shown in Tables 6 and 7a–7c.

TABLE 7

Oligonucleotide primer pairs to amplify any enteric dgt gene sequence

| Pair No. | Sequence | SEQ ID NO: | Position in SEQ ID NO:1 | Amplified DNA Length (bp) |
|---|---|---|---|---|
| 1 | CCACTGGAGCGCAATG | 2 | 166–181 | 184 |
| 1 | TGCATCAGGCATGACAT | 3 | 334–350 | 184 |
| 2 | CCACTGGAGCGCAATG | 2 | 166–181 | 215 |
| 2 | AAAATGACCAAACGGCGG | 4 | 364–381 | 215 |
| 3 | GGGCGCTACATCGC | 5 | 229–242 | 121 |
| 3 | TGCATCAGGCATGACAT | 3 | 334–350 | 121 |
| 4 | GGGCGCTACATCGC | 5 | 229–242 | 152 |
| 4 | AATGACCAAACGGCGG | 6 | 364–381 | 152 |

TABLE 8a

Oligonucleotide primer pairs to specifically amplify *Escherichia coil* dgt nucleic acids

| Pair No. | Sequence | SEQ ID NO: | Position in SEQ ID NO:1 | Amplified DNA Length (bp) |
|---|---|---|---|---|
| 5 | GCTGCAGCGTGGCGGCA | 7 | 461–477 | 213 |
| 5 | CTCAGGCGTTTCGCCACG | 8 | 656–673 | 213 |
| 6 | CCCGGAAGATGCCGAAA | 9 | 423–439 | 251 |
| 6 | CTCAGGCGTTTCGCCACG | 8 | 656–673 | 251 |
| 7 | CCCGGAAGATGCCGAAA | 9 | 423–439 | 82 |
| 7 | CGGTTCTTCCCCGTCCC | 10 | 488–504 | 82 |

TABLE 8b

Oligonucleotide primer pairs to specifically amplify *Salmonella typhymurium* nucleic acids

| Pair No. | Sequence | SEQ ID NO: | Position in SEQ ID NO:1 | Amplified DNA Length (bp) |
|---|---|---|---|---|
| 8 | GCTGTGTGGTTTCCTCG | 11 | 461–477 | 213 |
| 8 | AATCCGGCACCGGCCCTC | 12 | 656–673 | 213 |
| 9 | TCCGGAAGATGCGGAAA | 13 | 423–439 | 251 |
| 9 | AATCCGGCACCGGCCCTC | 12 | 656–673 | 251 |

TABLE 8b-continued

Oligonucleotide primer pairs to specifically amplify *Salmonella typhymurium* nucleic acids

| Pair No. | Sequence | SEQ ID NO: | Position in SEQ ID NO:1 | Amplified DNA Length (bp) |
|---|---|---|---|---|
| 10 | TCCGGAAGATGCGGAAA | 13 | 423–439 | 82 |
| 10 | ATTTTCTTCACCTTCCT | 14 | 488–504 | 82 |

TABLE 8c

Oligonucleotide primer pairs to amplify *Klebsiella oxytoca* nucleic acids

| Pair No. | Sequence | SEQ ID NO: | Position in SEQ ID NO:1 | Amplified DNA Length (bp) |
|---|---|---|---|---|
| 11 | GCTGCGAAGTGCAGGCC | 15 | 461–477 | 213 |
| 11 | TGGCCGGCGTCTCCTCAG | 16 | 656–673 | 213 |
| 12 | GCCCGGCGATGCGCTCG | 17 | 423–439 | 251 |
| 12 | TGGCCGGCGTCTCCTCAG | 16 | 656–673 | 251 |
| 13 | GCCCGGCGATGCGCTCG | 17 | 423–439 | 82 |
| 13 | CGATGTCTCTCCGTCAT | 18 | 488–504 | 82 |

Polymerase chain reaction (PCR) amplification of DNA was performed using VENT thermopolymerase from New England Biolabs, Inc. according to the instructions provided by the manufacturer. All PCR reactions were carried out in a ProGene thermocycler from Techne, Inc. In general, the amplification products were visualized after size separation on a 1.2% agarose gel by staining with ethidium bromide.

Figure 10:
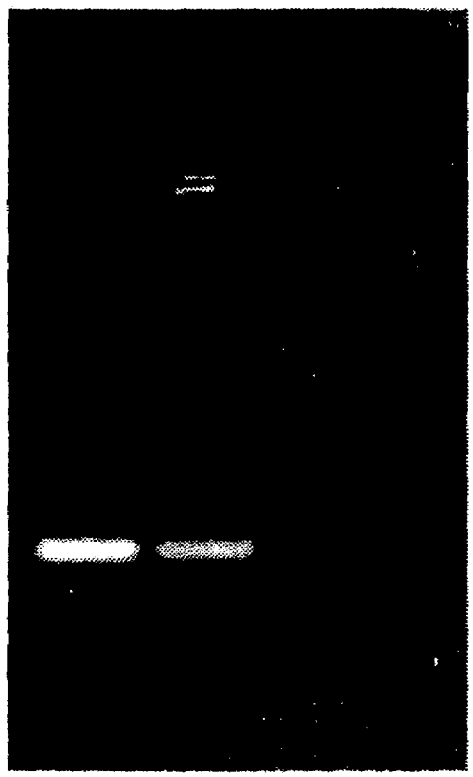
FIG. 10 illustrates that the methods of the invention can detect as few as 100 Enterobacteriaceae (in this case *E. coli*) in a test sample. Primer set 1 was used to amplify the 184 bp fragment from approximately 1000 *E. coli* bacteria (lane 1), 100 bacteria (lane 2), and 10 bacteria (lane3). Thirty cycles of the PCR reaction were employed. The band in lane 3 is just visible in the original gel. The gel is 1.2% agarose and is stained with ethidium bromide.

FIG. 10 illustrates that the methods of the invention can detect as few as 10 to 100 Enterobacteriaceae in a test sample. Primer set 1 was used to amplify a 184 bp fragment from approximately 1000 *E. coli* bacteria in lane 1, from approximately 100 *E. coli* bacteria in lane 2, and from approximately 10 *E. coli* bacteria in lane3. Only thirty cycles of the PCR reaction were performed. The band in lane 3 is just visible in the original gel, where only about 10 copies of template DNA were present.

Figure 11:
FIG. 11 illustrates the specificity of the nucleic acid probes provided by the invention. In this experiment, DNA was obtained from approximately 200 cfu from various species of Enterobacteriaceae. These DNA isolates were subjected to PCR amplification using primer set 5 that specifically amplify only *E. coli* dgt nucleic acids to produce a 213 bp fragment. The products of amplification were separated on a 1.2% agarose gel and stained with ethidium bromide. Each lane contains the amplification products from a separate genus of substrate DNA: Lane 1—*Klebsiella*; Lane 2—*Salmonella*; Lane 3—*Shigella*; Lane 4—*Yersinia*; Lane 5—*Escherichia*. The 213 bp fragment is correctly amplified only in the *E. coli* lane.

The primers provided in Tables 7a–7c are specific for the indicated genus of Enterobacteriaceae. FIG. 11 illustrates that primer set 5, that was designed to be specific for *Escherichia*, only amplifies DNA isolated from *Escherichia*. No DNA amplification was observed when the template DNA was from *Klebsiella, Salmonella, Shigella* or *Yersinia*.

Figure 12:
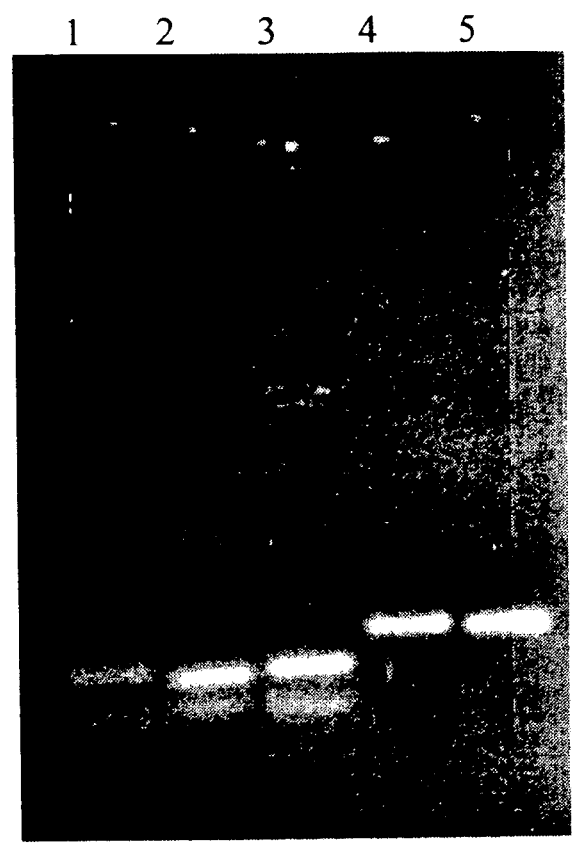
FIG. 12 further illustrates the specificity of the nucleic acid probes provided by the invention under conditions where different types of bacteria are present in the test sample and may compete for primer binding and amplification. In this experiment, DNA was obtained from approximately 200 cfu of two different genera of Enterobacteriaceae and mixed together. After amplification, the products were separated on a 1.2% agarose gel and stained with ethidium bromide. The species of bacterial DNA present in the samples and the primers used to test the specificity of amplification are provided below.

Moreover, the primers provided in Tables 7a–7c can still discriminate between DNA substrates, even when mixtures of DNA and more than one set of primers is present in the amplification reaction. As illustrated in FIGS. 12 and 13, designing the genus-specific primer sets so that bands of different lengths are amplified by each is one way to facilitate identification of the specific bacterial types in mixed cultures.

FIG. 12 shows that the genus-specific primers provided by the invention can discriminate between different types of Enterobacteriaceae DNA under conditions where different primers are present and may compete for primer binding and amplification. Mixtures of DNA obtained from approximately 200 cfu of two species of Enterobacteriaceae were amplified. The products were separated on a 1.2% agarose gel and stained with ethidium bromide. The species of bacterial DNA present in the samples and the primers used to test the specificity of amplification are provided below.

| Lane | Bacteria | Primer Pair | Band size (bp) |
|---|---|---|---|
| 1 | *Escherichia* + *Klebsiella* | 7 and 11 | 82 (*Escherichia*) + 213 (*Klebsiella*) |
| 2 | *Escherichia* + *Salmonella* | 7 and 8 | 82 (*Escherichia*) + 213 (*Salmonella*) |
| 3 | *Salmonella* + *Klebsiella* | 8 and 13 | 213 (*Salmonella*) + 82 (*Klebsiella*) |
| 4 | *Klebsiella* + *Escherichia* | 6 | 251 (*Escherichia*) |
| 5 | *Salmonella* + *Escherichia* | 6 | 251 (*Escherichia*) |

As shown in Tables 7a–7c, primer pairs 5, 6 and 7 were designed to be specific for *Escherichia*; primer pairs 8, 9 and 10 were designed to be specific for *Salmonella*; primer pairs 11, 12 and 13 were designed to be specific for *Klebsiella*. Each of the primer pairs employed actually synthesized a fragment of the predicted size for a particular genus of bacteria. Thus, the methods of the invention discriminate between DNA from related Enterobacteriaceae and correctly identify which bacterial genus is present in a mixed bacterial culture. FIG. 12 shows that the primer sets can be used in combination to amplify dgt sequence from bacteria in mixed cultures.

When multiple bands were visualized (as in FIG. 12, lane 1 for example) it is straightforward to make the identification. Finally the PCR based test can be used to amplify dgt genetic material from field samples. FIG. 13 shows the results from a series of amplifications using multiple primers. The sample was the fluid found in the bottom of a sealed package of commercial chicken. The results clearly indicate that the fluid contains measurable amounts of enteric bacteria (lanes 1 and 7), that it is *Escherichia* (lanes 2 and 6), not *Klebsiella* (lane 3), and that it is *Salmonella* (lanes 4 and 5). This result also indicates that the PCR based test does not amplify spurious materials as evidenced by the lack of extra bands in the individual lanes, and that the test is not inhibited by serum or other components in the fluid.

REFERENCES

1. Foegeding, P. M. (1994). Council for Agricultural Science and Technology. Task Force Report. 1221.
2. Bunning, V. K., Lindsay, J. A., and Archer, D. L. (1997). Chronic health effects of microbial food borne disease. World Health Stat Quart. 50:51–56.
3. Linsay, J. A. (1998). Chronic squelae of food borne disease. Emerging Infect Diseases. 3:443–452.
4. Archer, D. L., and Young, F. E. (1988). Contemporary issues: diseases with a food vector. Clin Microbiol Revs. 1:377–398.
5. Kaferstein, F. K., Motarjemi, Y., and Bettcher, D. W. (1998) Foodborne disease control: a transnational challenge. Emerging Infect Diseases. 3:503–510.
6. Nataro, J. P., Steiner, T., and Guerrant, R. L. (1998). Enteroaggregative *Escherichia coli*. Emerg Infect Diseases. 4:251–261.
7. Olsvik, O., Wasteson, Y., Lund, A., and Homes. (1991). E. Pathogenic *Escherichia coli* found in food. Int. J. Food Microbiol. 12:103–113.
8. World Health Organization Expert Committee on Food Saftey. WHO Tech Rep Ser 705 1984.
9. Ochman, H., and Wilson, A. C. Evolutionary history of enteric bacteria, p. 1649–1654. in *Escherichia coli* and Salmonella typhimurium: cellular and molecular biology, Neidhardt, F. C., Ingraham, J. L., Low, K. B., Magasanik, B., Schaechter, M., and Umbarger, H. E., eds. American Society for Microbiology, Washington, D.C. 1987.

10. Jackson, L. A., and Wenger, J. D. (1983). Listeriosis: a food borne disease. Infects In Med. 10: 61–66.

11. Dekeyser, P. J., Gossip-Detrain, M., Butler, J. P., and Sterno, J. (1972). Acute enteritis due to related vibrio: first positive stool cultures. J Infect Dis. 125: 390–392.

12. Quirk, S. and Bessman, M. J. (1991). Deoxyguanosine triphosphate triphosphohydrolase, a unique enzyme confined to members of the family Enterobacteriaceae. J Bact. 173: 6665–6669.

13. Seto, D., Bhaunagar, S. K., and Bessman, M. J. (1988). The purification and properties of deoxyguanosine triphosphate triphosphohydrolase from *Escherichia coli*. J Biol. Chem. 263:1494–1499.

14. Beauchamp, B. B., and Richardson, C. C. (1988). A unique deoxyguanosine triphosphatase is responsible for the optA1 phenotype. Proc Natl Acad Sci USA. 85: 2563–2567.

15. Kornberg, S. R., Lehman, I. R. Bessman, M. J., Simms, E. S., and Kornberg, A. (1958). Enzymatic cleavage of deoxyguanosine triphosphate to deoxyguanosine and tripolyphosphate. J Biol. Chem. 233:159–162.

16. Quirk, S. and Do, B. T. (1997). Cloning, Purification and characterization of the *Shigella Boydii* dGTP triphosphohydrolase. J Biol Chem 1997; 272: 332–336.

17. Li, C. and Clarke S. (1992). Distribution of an L-Isoaspartyl protein methyltransferase in Eubacteria. J Bact 1992; 174:355–361.

18. Miller, J. H. (1972). Experiments in Molecular Genetics. Cold Spring Harbor Laboratory, Cold Spring Harbor, N.Y.

19. Bradford, M. M. (1976). A rapid and sensitive method for the quantitation of microgram quantities of protein utilizing the principle of dye binding. Anal. Biochem. 72, 248–254.

20. Nakai, H. and Richardson CC. (1990). The gene 1.2 protein of bacteriophage T7 interacts with the *Escherichia coli* dGTP triphosphohydrolase to form a GTP binding protein. J. Biol. Chem. 265, 4411–4419.

21. Siegel, L M., and Monty, K. J. (1966). Determination of molecular weights and frictional ratios of proteins in impure systems by the use of gel filtration and density gradient centrifugation. Application to crude preparations of sulfite and hydroxylamine reductases. Biochim. Biophys. Acta 112, 346–362.

22. Laemmli, U. K. (1970). Cleavage of structural proteins during the assembly of the head of bacteriophage T4. Nature (London) 227, 680–685.

23. Wurgler, S. M., and Richardson, C. C. (1990). Structure and regulation of the gene for dGTP triphosphohydrolase from *Escherichia coli*. Proc. Natl. Acad. Sci. U.S.A. 87, 2740–2744.

24. Kaiser, D. A. and Pollard, T. D. (1996). Characterization of actin and poly-L-proline binding sites of Acanthaoemba profilin with monoclonal antibodies and by mutagenesis. J. Mol. Biol. 255, 89–107.

25. Quirk, S., Maciver, S. K., Ampe, C., Doberstein, S. K., Kaiser, D. A., VanDamme, J., Vandekerckhove, J S., and Pollard, T. D. (1993). Primary structure of and studies on Acanthamoeba actophorin. Biochemistry, 32: 8525–8533.

26. Towbin, H., Staehelin, T., Gordon, J. (1979). Electrophoretic transfer of proteins from polyacrylamide gels to nitrocellulose sheets: procedure and some applications. Proc. Nat. Acad. Sci., U.S.A. 76, 4350–4354.

27. Lofas, S., B. Johnsson, A. Edstrom, A. Hansson, G. Lindquist, R-M Muller Hillgren, and L. Stigh. (1995). Methods for site controlled coupling to carboxymethyl-dextran surfaces in surface plasmon resonance sensors Biosensors & Bioelectronics 10, 813–822.

28. Stainer, R. Y., Ingrham, J. L., Wheelis, M. L., and Painter, P. R. (1986). The Microbial World, 5th edition. Prentice Hall, Englewood Cliffs, N.J.

29. Belgrader, P., Benett, W., Hadley, D., Long, D., Mariella, R., Milanovich, F., Nasarabadi, S., Nelson, W., Richards, J., and Stratton, P. (1998). Rapid pathogen detection using a microchip PCR array instrument. Clin. Chem. 44, 2191–2194.

30. Haedicke, W., Wolfe, H., Ehret, W., Reischl, U. (1996) Specific and sensitive 2-step polymerase chain reaction assay for the detection of *Salmonella* species. Eur. J. Clin. Micrbiol. Infect. Dis. 15, 603–607.

31. Northrup, M. A., Benett, B., Hadley, D., Landre, P., Lehew, S., Richards, J., and Stratton, P. A. (1998) A miniature analytical instrument for nucleic acids based on micromachined silicon reaction chambers. Anal. Chem. 70, 918–922.

32. Dubs, M. C., Altschuh, D., and van Regenmortel, M. H. V. (1991). Interaction between viruses and monoclonal antibodies studied by surface plasmon resonance. Immunol. Letters 31, 59–64.

33. Karlsson, R., Michaelsson, A., and Mattson, L. (1991). Kinetic analysis of monoclonal antibody-antigen interactions with a new biosensor based analytical system. J. Immunol. Meths. 145, 229–2440.

34. Raether, H. Surface Plasmons. Springer, Berlin. 1988.

35. Levasseur, S., Husson, M. O., Leitz, R., Merlin, R., Laurent, F., Peladan, F., Drocourt, J. L., Leclerc, H., and Van Hoegaerden, M. (1992). Rapid detection of members of the family Enterobacteriaceae by a monoclonal antibody. Appl. Environ. Microbiol. 58, 1524–1529.

36. Quinlan, J. J., Foegeding, P. M. (1997). Monoclonal antibodies for use in detection of *Bacillus* and *Clostridium* spores. Appl Environ Microbiol. 63, 482–487.

37. Sojka, M. G., Dibb-Fuller, M., and Thoms, C. J. (1996). Characterization of monoclonal antibodies specific to SEF21 fimbriae of *Salmonella enteritidis* and their reactivity with other *salmonellae* and *enterobacteria*. Vet. Microbiol. 48, 207–221.

38. Kaferstein, F. K., Motarjemi, Y., and Bettcher, D. W. (1998). Food borne disease control: a transnational challenge. Emerging Infect. Diseases. 3: 503–510.

39. Schaberg, D. R., and Culver, D. H. (1991). Major trends in the etiology of nosocomial infection. Am. J. Med. 91, (Suppl 3B), 72–75.

40. Janda, J. M., and Abbott, S. L. (1993). Infections associated with the genus *Edwardsiella*: The role of *Edwardsiella tarda* in human disease. Clin. Infect. Dis. 17, 742–748.

41. Frasch, C. (1997). Serogroup and serotype classification of bacterial pathogens. In Bacterial Pathogenesis, Academic Press, New York.

42. Janda, J. M., and Abbott, S. L. The Enterobacteria. Lippincott-Raven, Philadelphia 1998.

What is claimed:

1. An isolated nucleic acid that consists of SEQ ID NO:11, SEQ ID NO:12, SEQ ID NO:13, or SEQ ID NO:14.

2. A biosensor chip that comprises a nucleic acid that consists of SEQ ID NO:11, SEQ ID NO:12, SEQ ID NO:13, or SEQ ID NO:14.

3. A method of detecting the presence of enteric bacteria in a test sample that comprises contacting the test sample with a probe under stringent hybridizations conditions, and detecting hybridization between the probe and a nucleic acid in the test sample, wherein the probe consists of SEQ ID NO:11, SEQ ID NO:12, SEQ ID NO:13, or SEQ ID NO:14.

4. The method of claim 3 wherein the enteric bacteria are of the family Enterobacteriaceae.

5. The method of claim 3 that further comprises DNA amplification.

6. The method of claim 5 wherein the DNA amplification is by polymerase chain reaction.

7. A method of detecting the presence of *Salmonella* in a test sample that comprises contacting the test sample with a probe under stringent hybridizations conditions, and detecting hybridization between the probe and a nucleic acid in the test sample, wherein the probe comprises isolated nucleic acid that consists of SEQ ID NO:11, SEQ ID NO:12, SEQ ID NO:13, or SEQ ID NO:14.

8. The method of claim 7 wherein the probe selectively hybridizes to DNA from *Salmonella typhymurium* in the presence of DNA from *Klebsiella* or *Escherichia*.

9. The method of claim 7 that further comprises DNA amplification.

10. The method of claim 9 wherein the DNA amplification is by polymerase chain reaction.

11. A biosensor chip that comprises a solid support and a nucleic acid probe that can selectively hybridize to nucleic acid encoding a dGTPase from Enterobacteriaceae, wherein the probe is a nucleic acid consisting of SEQ ID NO:11, SEQ ID NO:12, SEQ ID NO:13 or SEQ ID NO:14.

* * * * *